US011207219B1

United States Patent
King et al.

(10) Patent No.: US 11,207,219 B1
(45) Date of Patent: Dec. 28, 2021

(54) CLIP ON ELECTRONICS MODULE

(71) Applicants: BioLink Systems, LLC, Covington, KY (US); University of Louisville Research Foundation, Inc., Louisville, KY (US)

(72) Inventors: Roger King, Hamilton, OH (US); Doug Jackson, New Albany, IN (US); John Naber, Goshen, KY (US); Jason Heyl, Cincinatti, OH (US)

(73) Assignee: BioLink Systems, LLC, Covington, KY (US)

( * ) Notice: Subject to any disclaimer, the term of this patent is extended or adjusted under 35 U.S.C. 154(b) by 0 days.

(21) Appl. No.: 17/245,007

(22) Filed: Apr. 30, 2021

Related U.S. Application Data

(63) Continuation of application No. 17/097,064, filed on Nov. 13, 2020, now Pat. No. 11,020,285.

(51) Int. Cl.
*G01R 31/28* (2006.01)
*A61F 13/42* (2006.01)
(Continued)

(52) U.S. Cl.
CPC ........ *A61F 13/42* (2013.01); *A61F 13/15577* (2013.01); *A61F 13/49* (2013.01); *H01R 43/16* (2013.01); *H01R 43/205* (2013.01); *A61F 2013/15121* (2013.01); *A61F 2013/421* (2013.01); *A61F 2013/424* (2013.01); *A61F 2013/8491* (2013.01); *H01R 4/2404* (2013.01);
(Continued)

(58) Field of Classification Search
CPC .... A61F 13/15577; A61F 13/42; A61F 13/49; H01R 43/16; H01R 43/205
See application file for complete search history.

(56) References Cited

U.S. PATENT DOCUMENTS

| 1,032,203 A | 7/1912 | Grinnell |
| 1,056,154 A | 3/1913 | Darby |

(Continued)

FOREIGN PATENT DOCUMENTS

| JP | 2017189348 | 10/2017 |
| WO | 2005015477 | 2/2005 |
| WO | 2008026123 | 3/2008 |

OTHER PUBLICATIONS

PCT-US2019-060421 International Search Report and Written Opinion, dated Mar. 12, 2020.
(Continued)

*Primary Examiner* — Paul D Kim
(74) *Attorney, Agent, or Firm* — Chris Tanner; TannerPatent.com

(57) ABSTRACT

A clip-on module having a specialized housing design, probe contacts, switches, various advertising modes, and various configurations of signal repeaters is disclosed. The module is utilized via attachment to a specialized garment worn by a human patient. To properly apply the housing to the garment, a user will squeeze the module to open using tactile features embedded within the housing, locate the module, and then press-clamp the module to close and attach it. A plurality of probe contacts within the module have sharpness requirements for penetrating one or more layers of the garment while still maintaining low resistance, and will work with a backing material for probe.

18 Claims, 31 Drawing Sheets

(51) Int. Cl.
*A61F 13/15* (2006.01)
*A61F 13/49* (2006.01)
*H01R 43/20* (2006.01)
*H01R 43/16* (2006.01)
H01R 12/70 (2011.01)
H01R 4/2404 (2018.01)
A61F 13/84 (2006.01)
H01R 4/247 (2018.01)

(52) U.S. Cl.
CPC .......... *H01R 4/247* (2013.01); *H01R 12/7076* (2013.01); *H01R 12/7082* (2013.01); *H01R 2201/12* (2013.01); *H01R 2201/20* (2013.01)

(56) References Cited

U.S. PATENT DOCUMENTS

| | | | |
|---|---|---|---|
| 1,071,337 A | 8/1913 | Phelps | |
| 5,416,469 A * | 5/1995 | Colling | A61B 5/202 |
| | | | 128/885 |
| 5,557,263 A | 9/1996 | Fisher et al. | |
| 6,246,330 B1 * | 6/2001 | Nielsen | A61F 13/42 |
| | | | 340/384.1 |
| 7,053,781 B1 | 5/2006 | Haire et al. | |
| 7,081,807 B2 * | 7/2006 | Lai | G08B 21/24 |
| | | | 340/309.7 |
| 7,559,902 B2 | 7/2009 | Ting et al. | |
| 7,977,529 B2 | 7/2011 | Bergman et al. | |
| 7,996,148 B2 | 8/2011 | Bergman et al. | |
| 8,145,422 B2 | 3/2012 | Bergman et al. | |
| 8,788,195 B2 | 7/2014 | Bergman et al. | |
| 9,107,776 B2 | 8/2015 | Bergman et al. | |
| 9,224,102 B2 | 12/2015 | Bergman et al. | |
| 9,283,123 B2 | 3/2016 | Bergman et al. | |
| 9,314,381 B2 | 4/2016 | Bergman et al. | |
| 9,646,073 B2 | 5/2017 | Bergman et al. | |
| 9,665,639 B2 | 5/2017 | Bergman et al. | |
| 9,713,554 B2 | 7/2017 | Bergman et al. | |
| 9,913,608 B2 | 3/2018 | Bergman et al. | |
| 10,533,733 B1 * | 1/2020 | Dewey | F21V 21/0965 |
| 10,786,210 B1 | 9/2020 | Heyl et al. | |
| 10,821,034 B2 | 11/2020 | Heyl et al. | |
| 10,940,484 B2 | 3/2021 | Heyl et al. | |
| 11,020,285 B1 | 6/2021 | King et al. | |
| 2008/0119244 A1 * | 5/2008 | Malhotra | H04M 1/0283 |
| | | | 455/575.1 |
| 2009/0005748 A1 * | 1/2009 | Ales | A61F 13/42 |
| | | | 604/361 |
| 2011/0001605 A1 | 1/2011 | Kiani | |
| 2011/0130174 A1 * | 6/2011 | Kroupa | H04M 1/15 |
| | | | 455/569.1 |
| 2011/0203954 A1 * | 8/2011 | Kroupa | A45F 5/004 |
| | | | 206/320 |
| 2013/0054467 A1 | 2/2013 | Dala et al. | |
| 2013/0282438 A1 | 10/2013 | Qaulcomm | |
| 2015/0257942 A1 | 9/2015 | Kim | |
| 2016/0095758 A1 | 4/2016 | Haire et al. | |
| 2016/0327253 A1 * | 11/2016 | Martinez | A61B 90/30 |
| 2020/0139076 A1 * | 5/2020 | Baillie | A61M 16/022 |

OTHER PUBLICATIONS

PCT-US2020-034439 International Search Report and Written Opinion, dated Sep. 10, 2020.
PCT-US2019-060421 International Preliminary Report on Patentability, dated Mar. 19, 2021.

\* cited by examiner

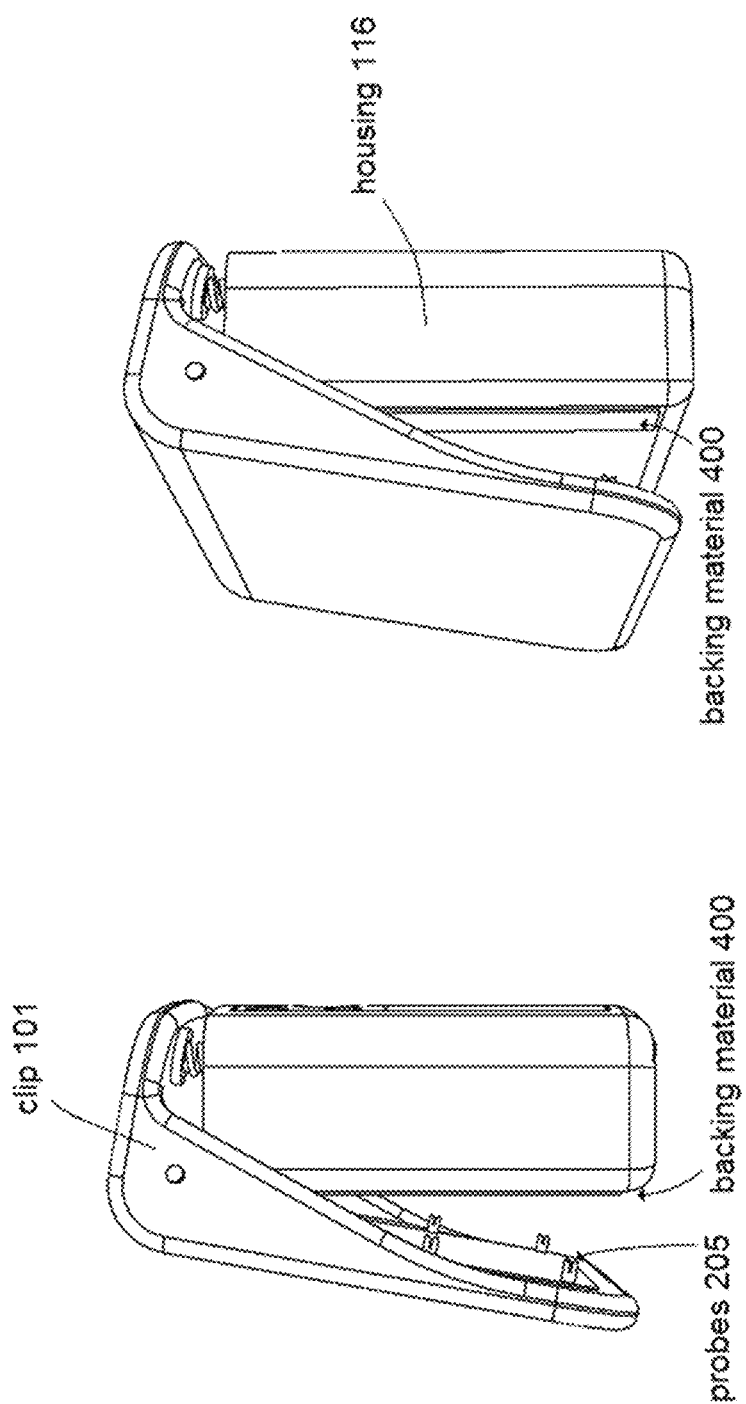

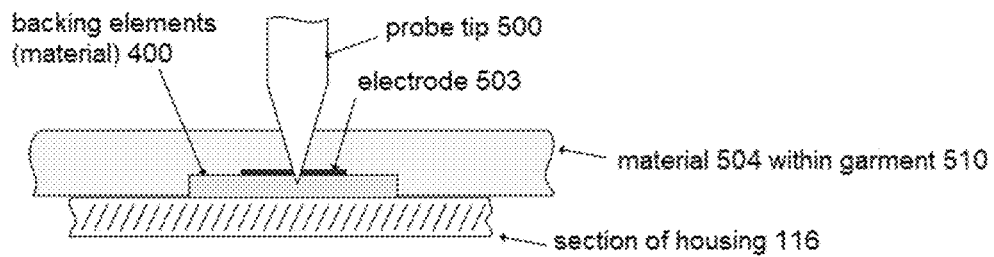
FIG. 5C (narrow taper)
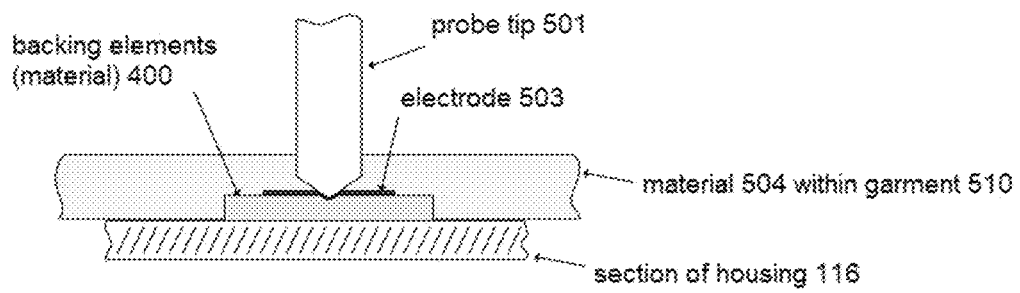
FIG. 5D (medium taper)
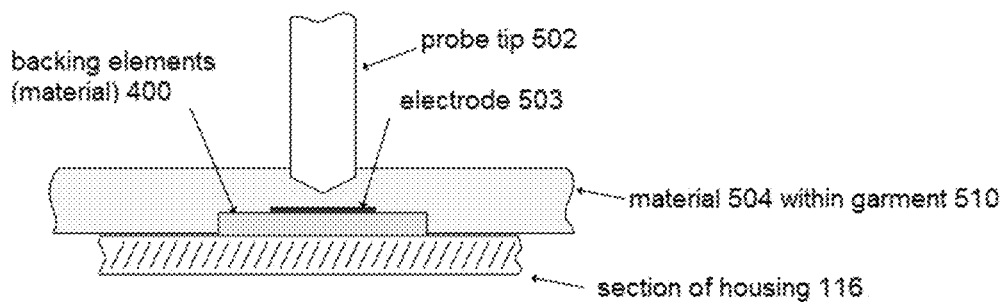
FIG. 5E (wide taper)

ABREF DESCRIPTION OF THE DRAWINGS# CLIP ON ELECTRONICS MODULE

CROSS REFERENCE TO RELATED APPLICATION

This application is a continuation of U.S. patent application Ser. No. 17/097,064, filed Aug. 25, 2018, now U.S. Pat. No. 11,020,285.

BACKGROUND OF THE INVENTION

Nursing homes and other residential facilities incur significant expense and difficulty in monitoring large amounts of patients who in many cases are aged, impaired, cannot communicate well, and also are losing control of their bowels and bladder. This situation can result in a lot of Urinary Tract Infections (UTIs) that can in turn result in expensive hospitalizations.

Accordingly, and system and method for tracking the health-conditions of large groups of patents is desired.

SUMMARY OF INVENTION

The embodiments herein comprise a clip-on module having a housing design, probe contacts, switches, various advertising modes, and various configurations of signal repeaters, for attachment to a specialized garment.

Specifically, the housing comprises a clip-on mode, a surface of housing having a viewable side and contact to skin-side, has features on clip that tightens top edge of brief when attached. To properly apply the housing, a user will squeeze the module to open using tactile features embedded within the housing, locate the module, and then press-clamp the module to close and attach it.

A plurality of probe contacts within the module have sharpness requirements for penetrating one or more layers of the garment while still maintaining low resistance, and will work with a backing material for probe.

The module further comprises sensors, temperature (contact and/or non-contact), accelerometer, skin conductivity, and numerous indicators. Switches and LEDs are located on the module for easy use by caregiver and to eliminate any requirement of other electronic devices being present during changing of a garment.

Within the module, advertisement modes can comprise advert mode only, combination mode advert and paired, and combination with Near Field Communication (NFC) for setup, polling, or other features.

An electronics module works with a specific type of and garment attaches over the center of the garment waistband by a clipping action. The module system is intended to provide a fast method of attachment, maintain secure attachment, provide comfortable wear including during multiple body positions, track body orientation, provide a means to contact conductive layers in the brief, provide a surface to contact the body, and provide a placement opportunity for sensors with exposure to a patient's skin.

BT advert repeaters can include devices, including a simple device with limited indicators. Advert repeater (portable or fixed) with data display, portable or fixed appliance (clock, night light, thermometer, other), repeating data, MAC address, company ID, group, sensor data, origin of data (first repeat hop, etc.), RSSI (signal intensity), BT traffic, whitelist/blacklist, user selected control, type of repeater, battery charge of repeater (assuming portable), command present in packet, data in packet in comparison to previously received data, time of day, commands sent via a special command advertisement by module or other device. Packet "idempotency token" (expiring code). Random delay code to prevent repeat collisions.

BRIEF DESCRIPTION OF THE DRAWINGS

FIGS. 4A, 4B, 4C, 4D, and 4E show the housing in an opened position;

FIGS. 5C, 5D, and 5E show cross section views of a probe penetrating garment inner layers over a conductive ink area;

DETAILED DESCRIPTION OF PREFERRED EMBODIMENTS

Figure 1A:
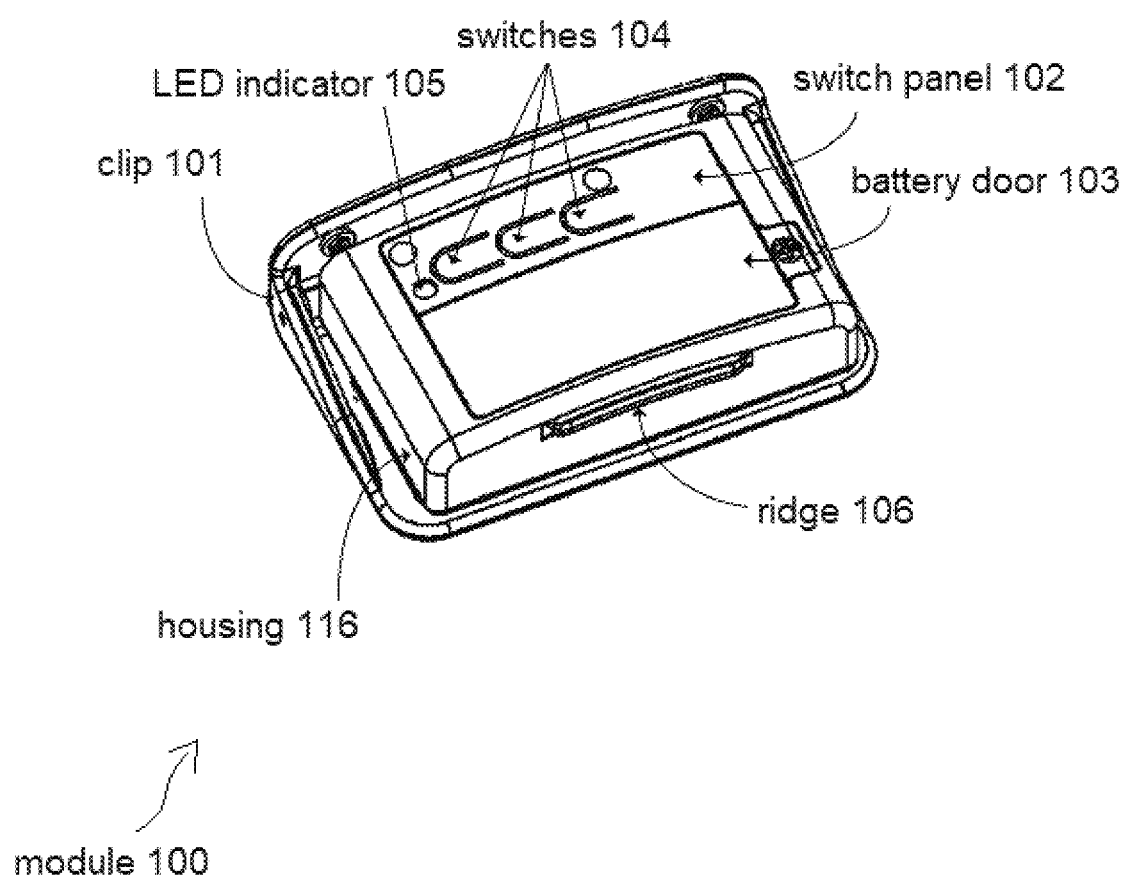
FIG. 1A shows a perspective view of the clip-on electronics module.

FIG. 1A shows a perspective view of the clip-on electronics module 100 for a garment 510 containing moisture sensing electrodes 503. Specifically, FIG. 1A shows a main housing 116 that houses the battery(s) and the majority of the electronics, a clip 101 portion that is placed over a waistband of the garment 510, a switch panel 102 that covers switches (buttons) 104 and LED indicator 105, and a battery door 103 for access to batteries within the module 100. A raised ridge 106 on the bottom of the main housing 116 provide tactile feedback and improves grip when squeezing the module 100 during attachment and removal. A companion and similar tactile feature is included on the top of clip 101 but for simplicity is not shown in FIG. 1A.

The housing 116 further comprises various labels that indicate functions of switches, indicate instructions, provide alignment hints, and model and branding data, but these will be better shown in other Figures and are thus excluded from FIG. 1A.

Figure 1B:
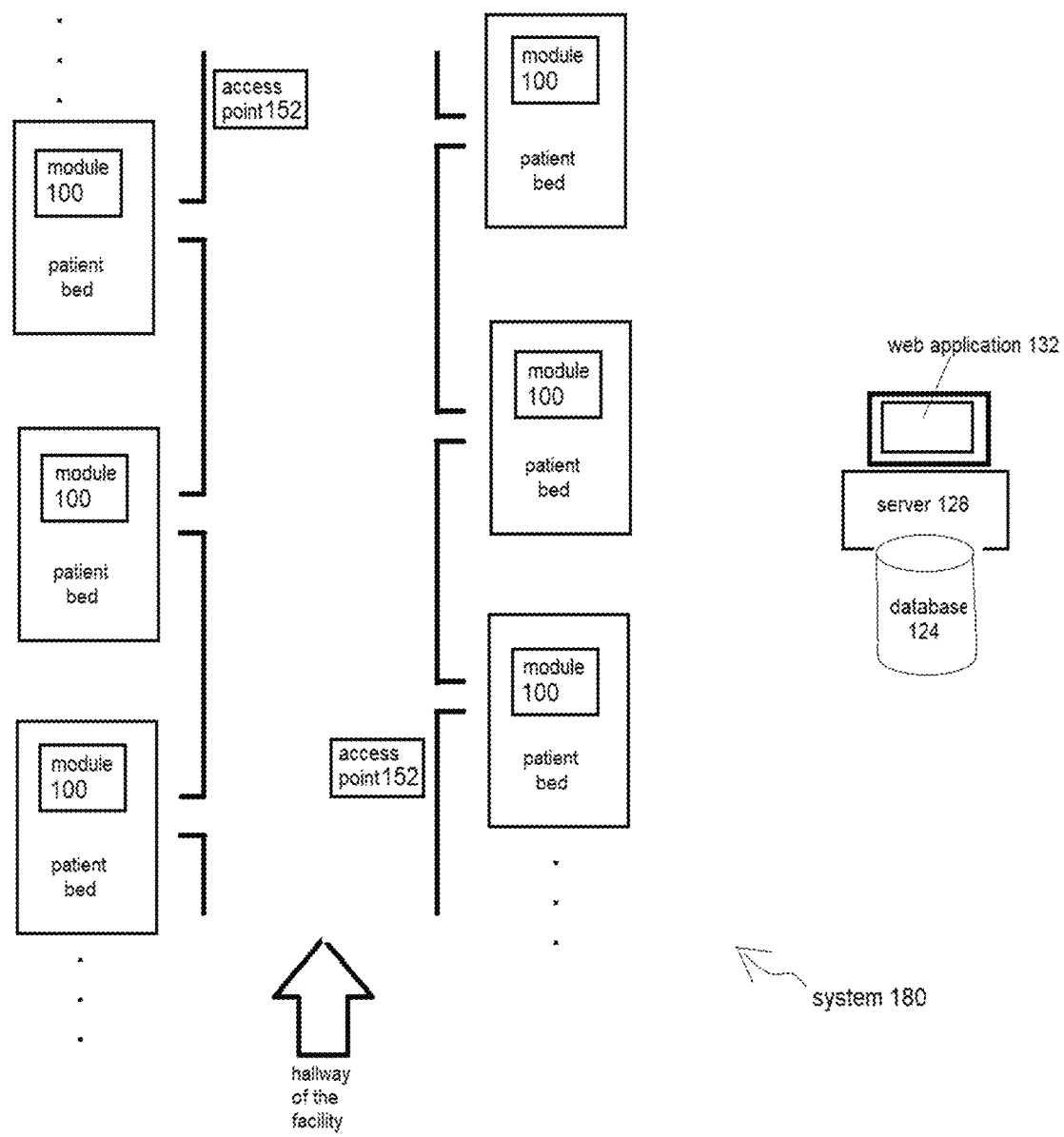
FIGS. 1B and 1C show topology/overviews of the module deployed in an actual-use environment.
Figure 1C:
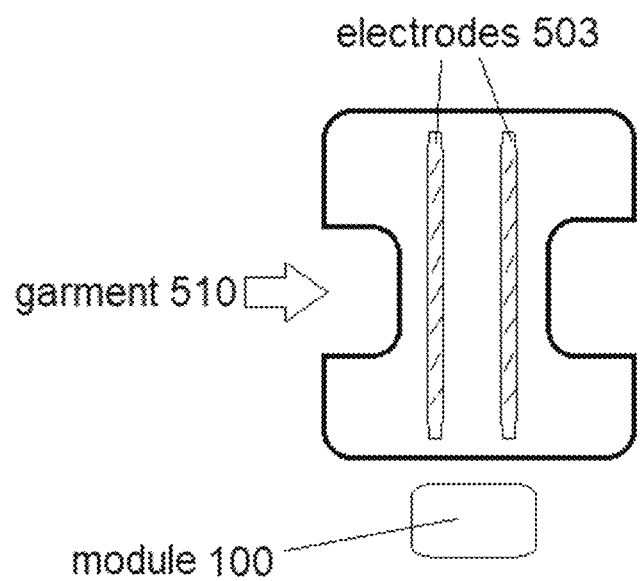

FIGS. 1B and 1C show a small overview of how the module 100 is employed. Some type of nursing home, residential facility, or other health-care facility with e.g. beds and patients can employ a system 180 in which patients are located in beds and each patient wears a module 100. A variety of access points 152 are strategically positioned to best relay the information detected by the module 100 to an example computer infrastructure comprising a server 128, a database 124, and a web application 132. FIG. 1C shows an example garment 510, in an embodiment shaped like a diaper, where the garment 510 has one or more electrodes 503 embedded therein, for detecting patient incontinence, among other conditions.

Figure 2A:
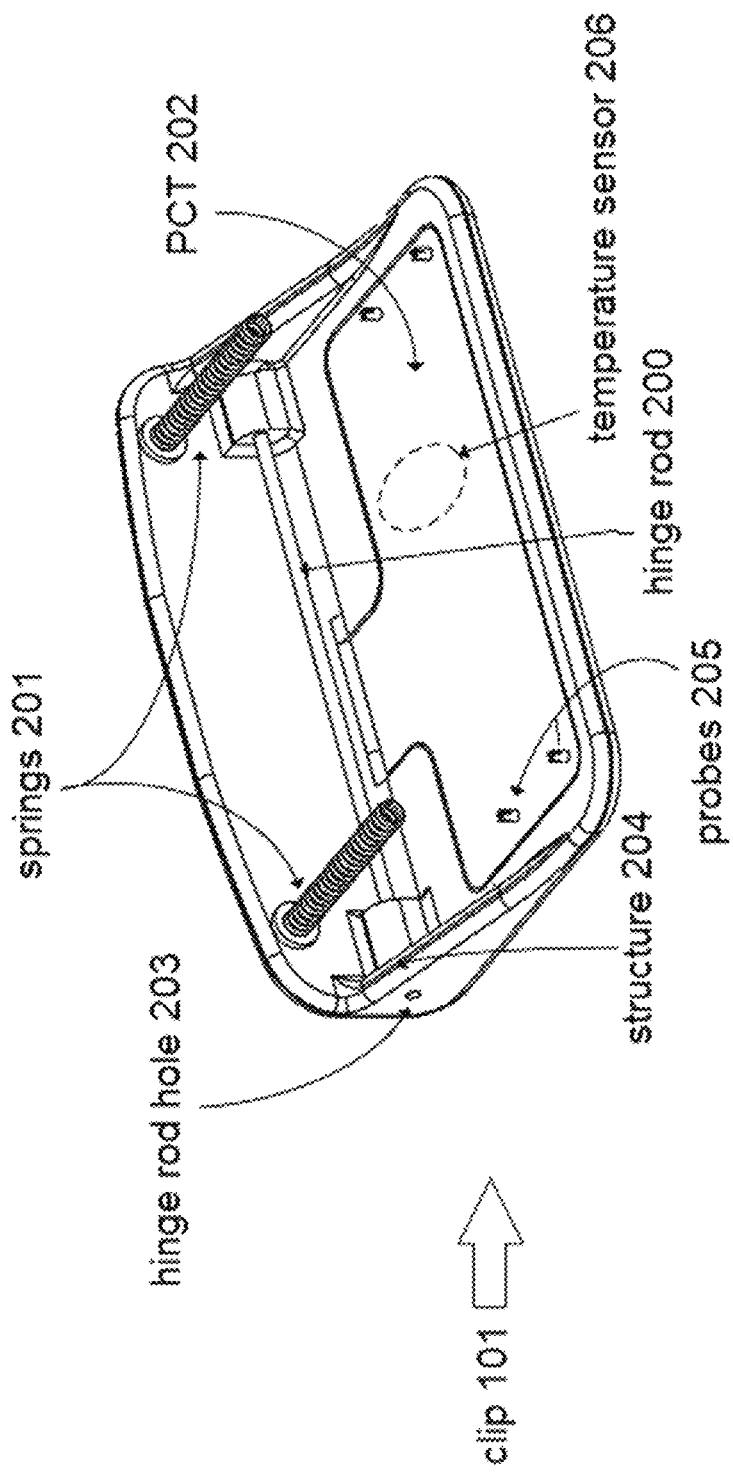
FIGS. 2A, 2C, and 2D show perspective views of a clip which is part of a housing.
Figure 2B:
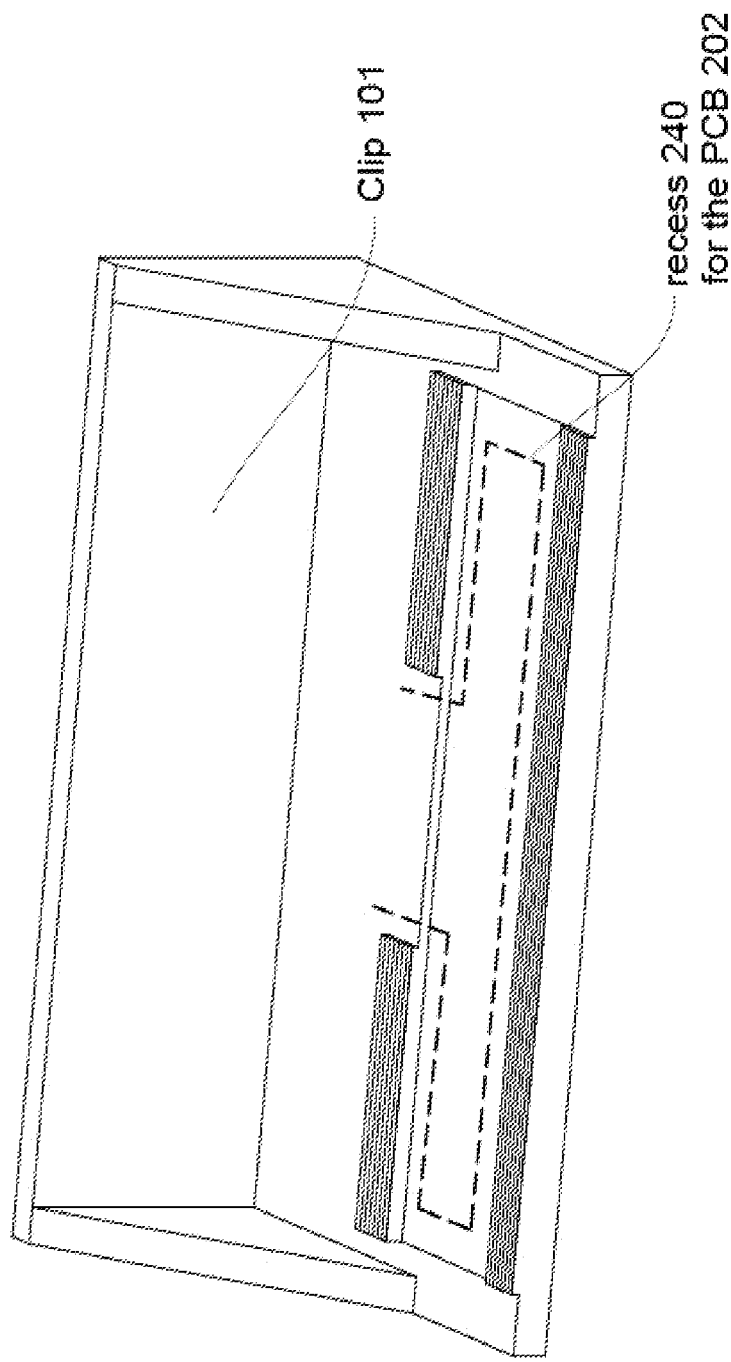
FIG. 2B shows a recess in the clip for locating a PCB.
Figure 2C:
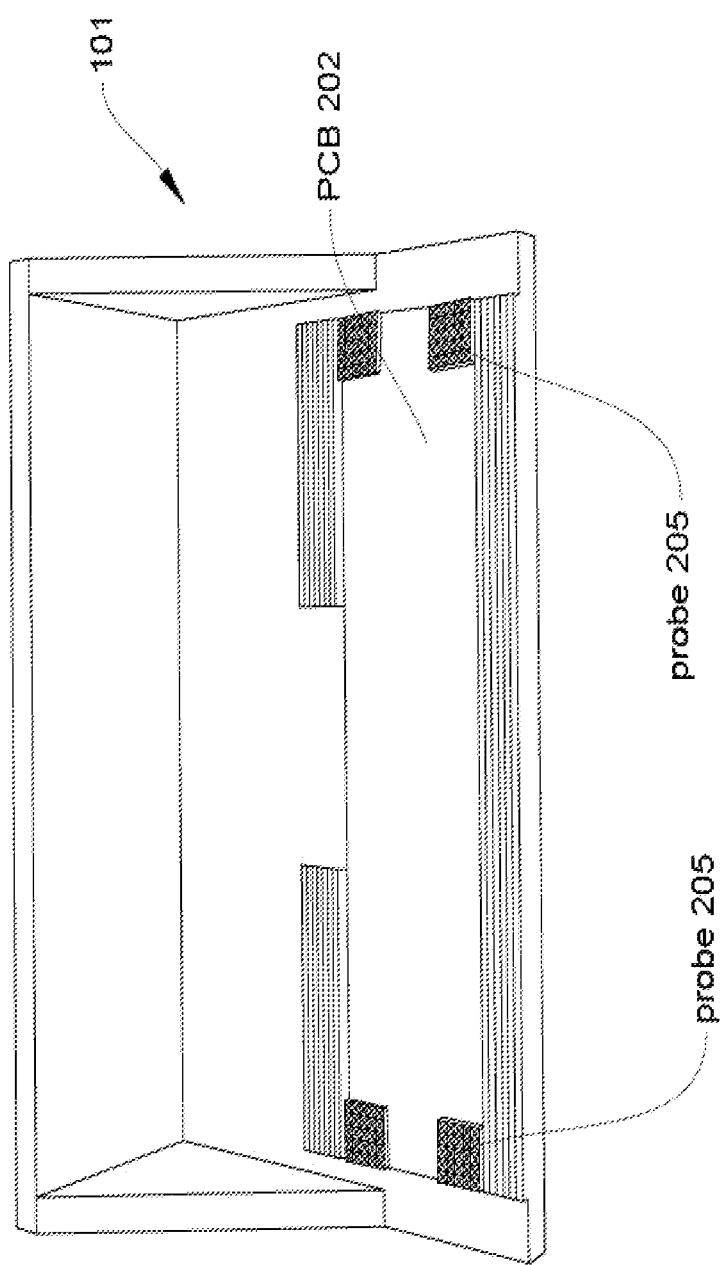
Figure 2D:
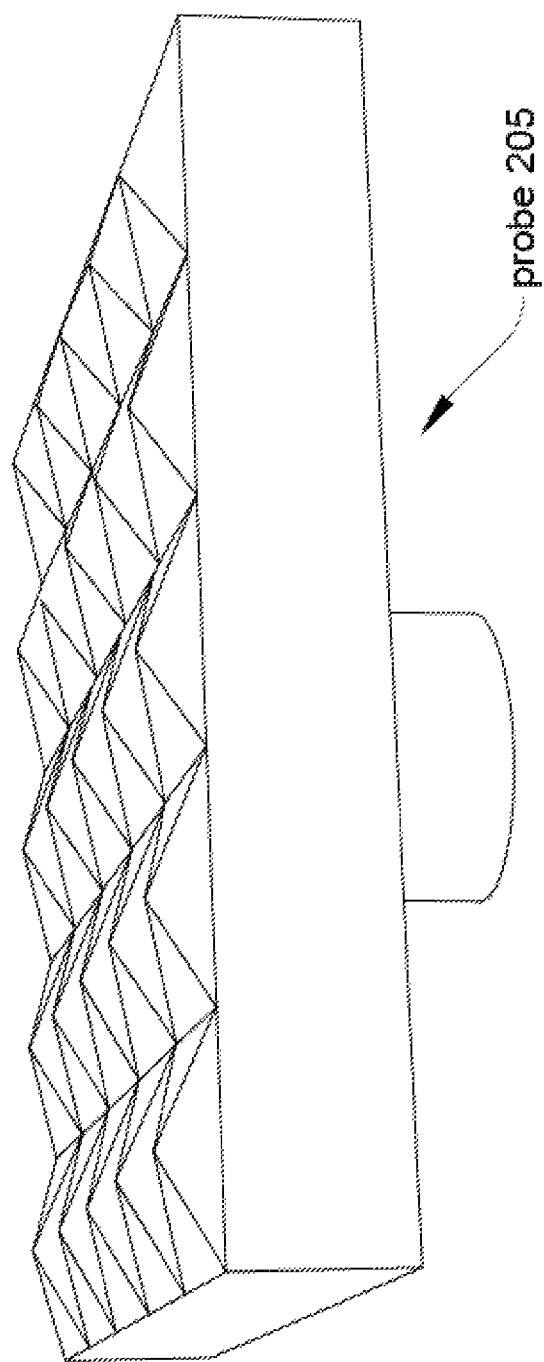

FIGS. 2A-2D show perspective views of the clip 101 and associated elements, for example, the probes 205. A metal hinge rod 200 is used to join the main housing 116 with the clip 101 and define a location and axis of rotation of the housing 116. Two coil springs 201 between the clip 201 and main housing 116 provide clamping force for securing the housing assembly to the garment 510 and to provide force for a plurality of probes 205 to contact the electrodes 503 within the garment 510. FIG. 2A shows four probes 205 as an example, but other numbers of probes 205 are also contemplated within the embodiments herein. A printed circuit board (PCB) 202 is used to hold the probes 205 and temperature sensor 206 located on the bottom of the printed circuit board 202. FIG. 2B shows a recess 240 for locating the PCB 202, which in an embodiment the PCB 202 may be in the form of a "stubby-T" shape.

Figure 2E:
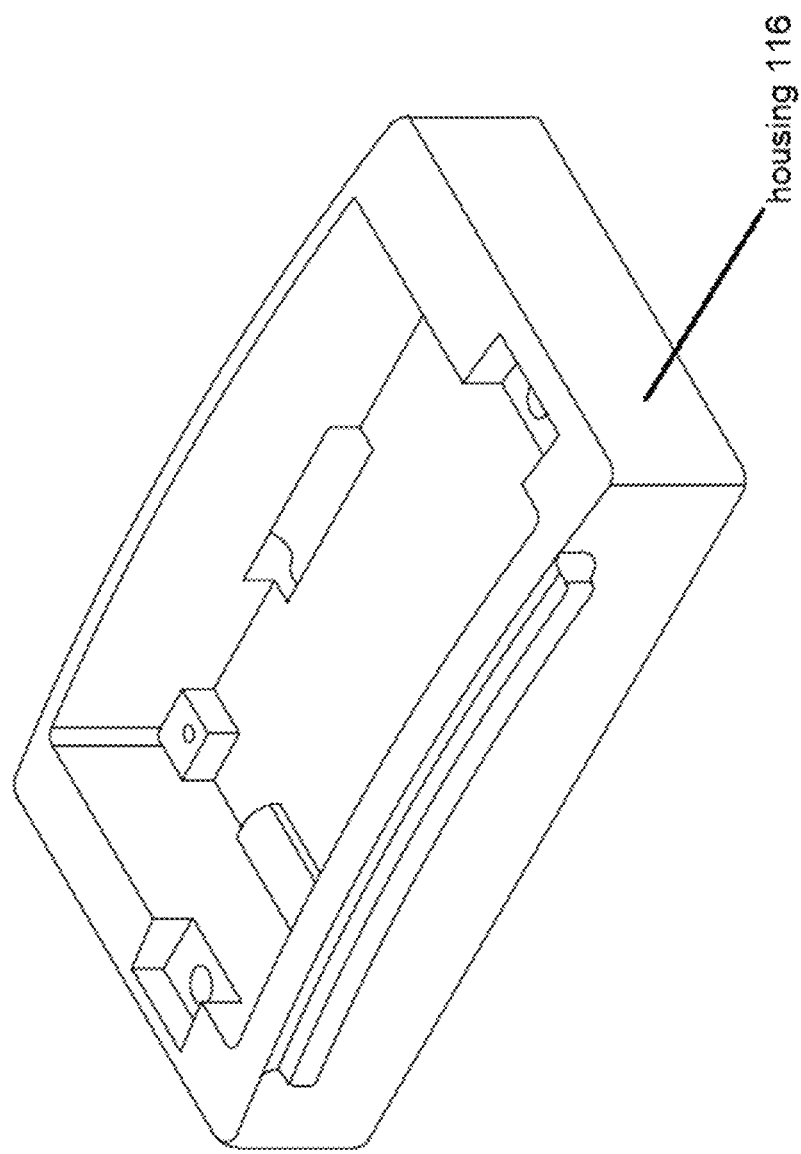
FIGS. 2E-2F show portions of the housing.
Figure 2F:
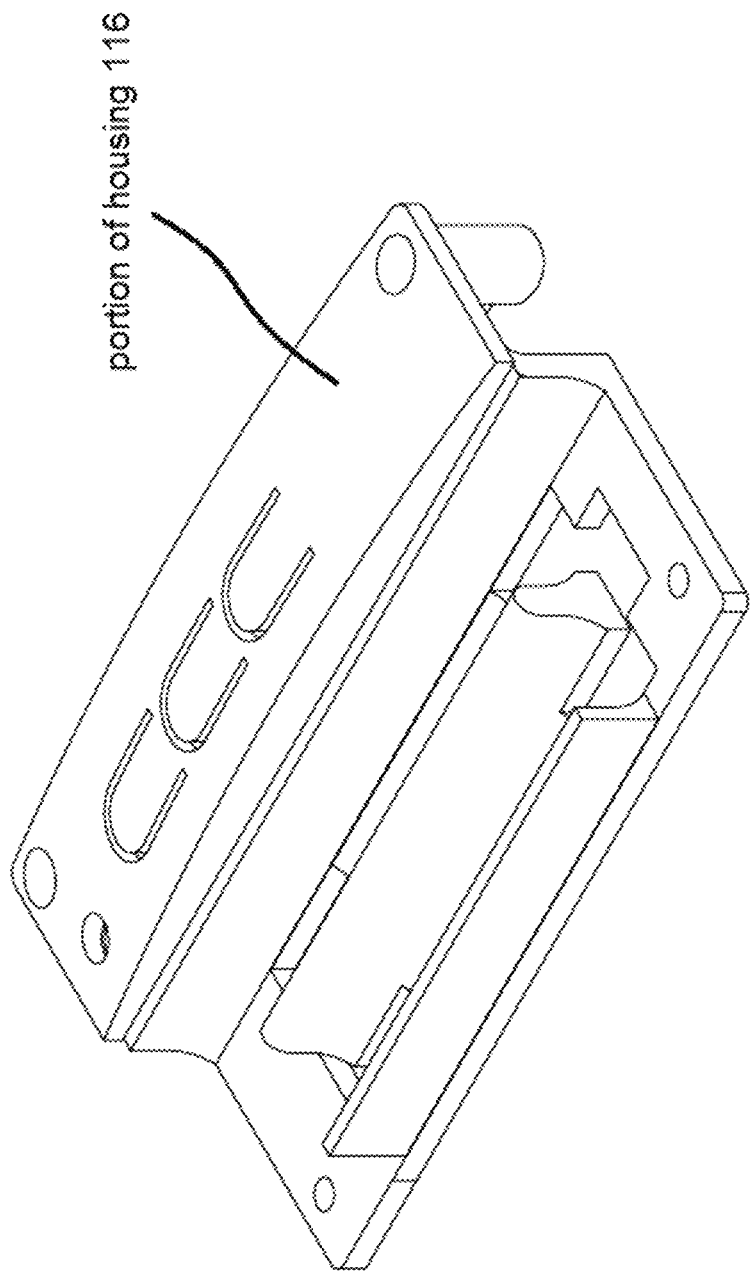

FIGS. 2E-2F show some potential implementations of the housing 116.

A clamping force of the module 100 may be adjustable through by changing the springs 201, adding a spacer to the end of the springs 201, or using a screw as a means to adjust the length of the pocket that the springs 201 rest in. Further, magnets could be used to replace or enhance clamping force provided by the springs 201. Next, a lever or screw could replace the springs for providing a means provide clamping pressure to the garment 510.

In an embodiment, it is possible to increase a finger size of a gripping area on the housing 116. It is also possible to increase a setback for the probes 205 from an edge of the housing 116. It is also possible to use of rubber disc vs stick-on-tape for the backing material 400 the probes 205 press into.

During use, the module 100 sometimes can tend to lean forward and pull away from the wearer's body. An excessive lean angle lessens the accuracy of the body position indication and moves the clip 101 farther from the wearer's body and thereby can at times reduce thermal conduction to the clip 101 that contains a temperature sensor 206. To address this, the structure 204 slightly tightens at a top edge of the waistband and reduces the lean angle of the module 100.

Figure 3:
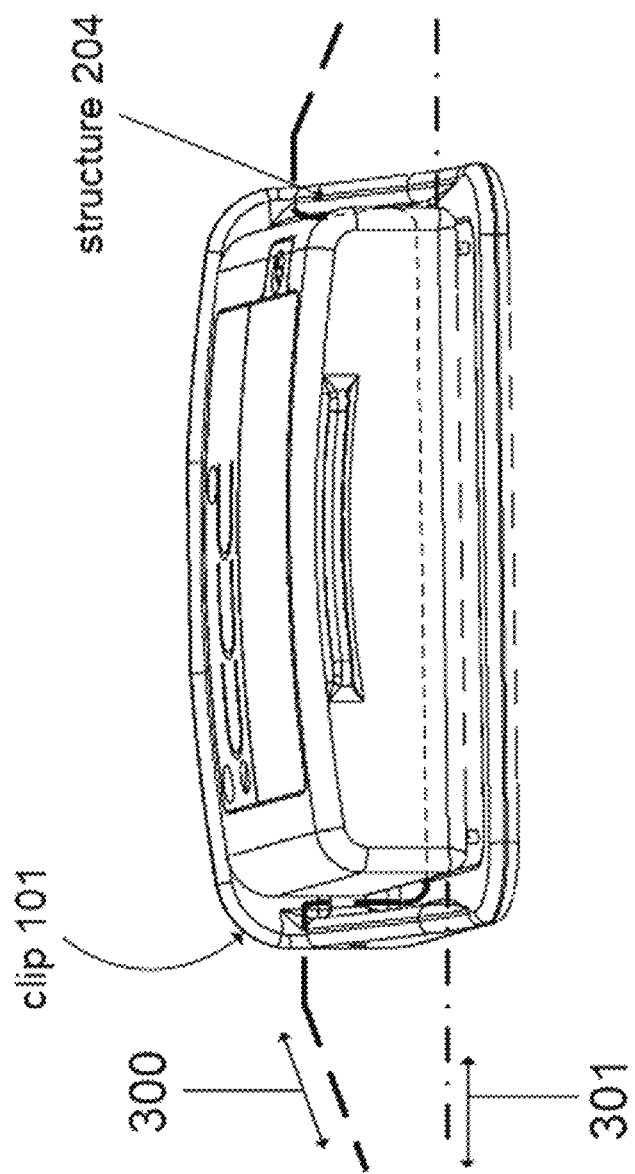
FIG. 3 shows a bottom view of the module.
Figure 4C:
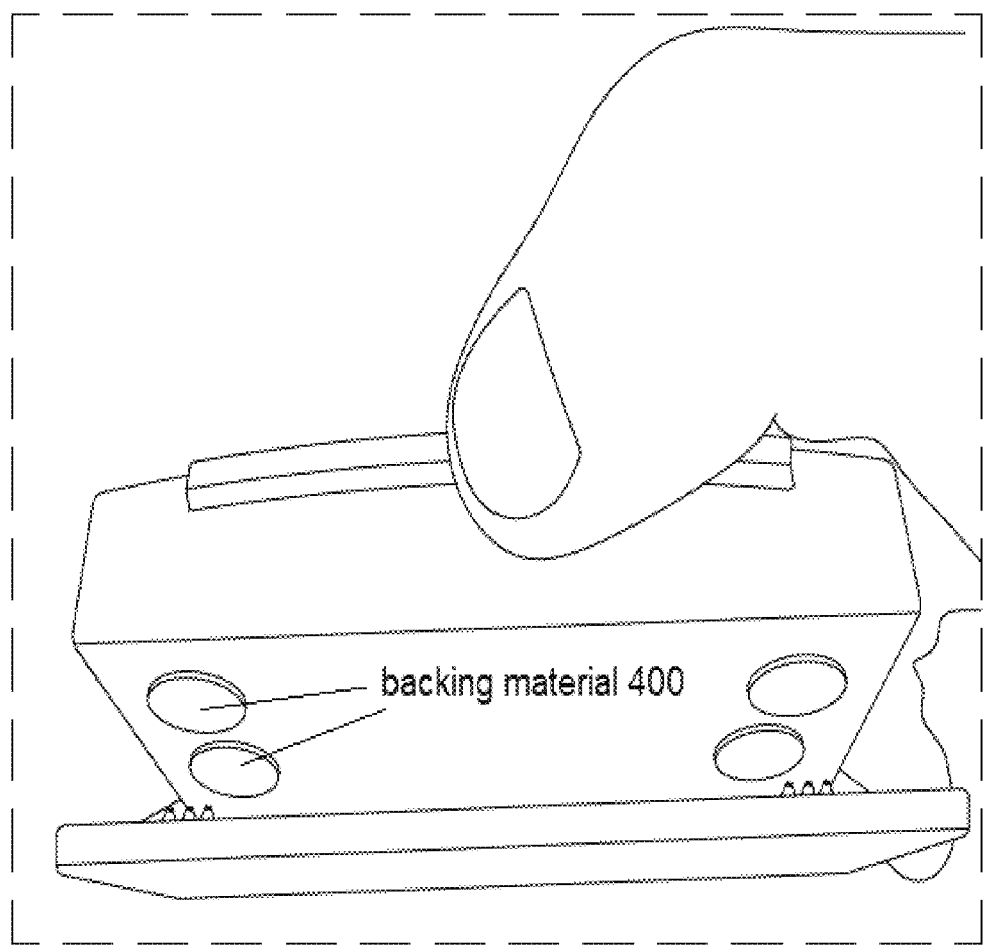
Figure 4D:
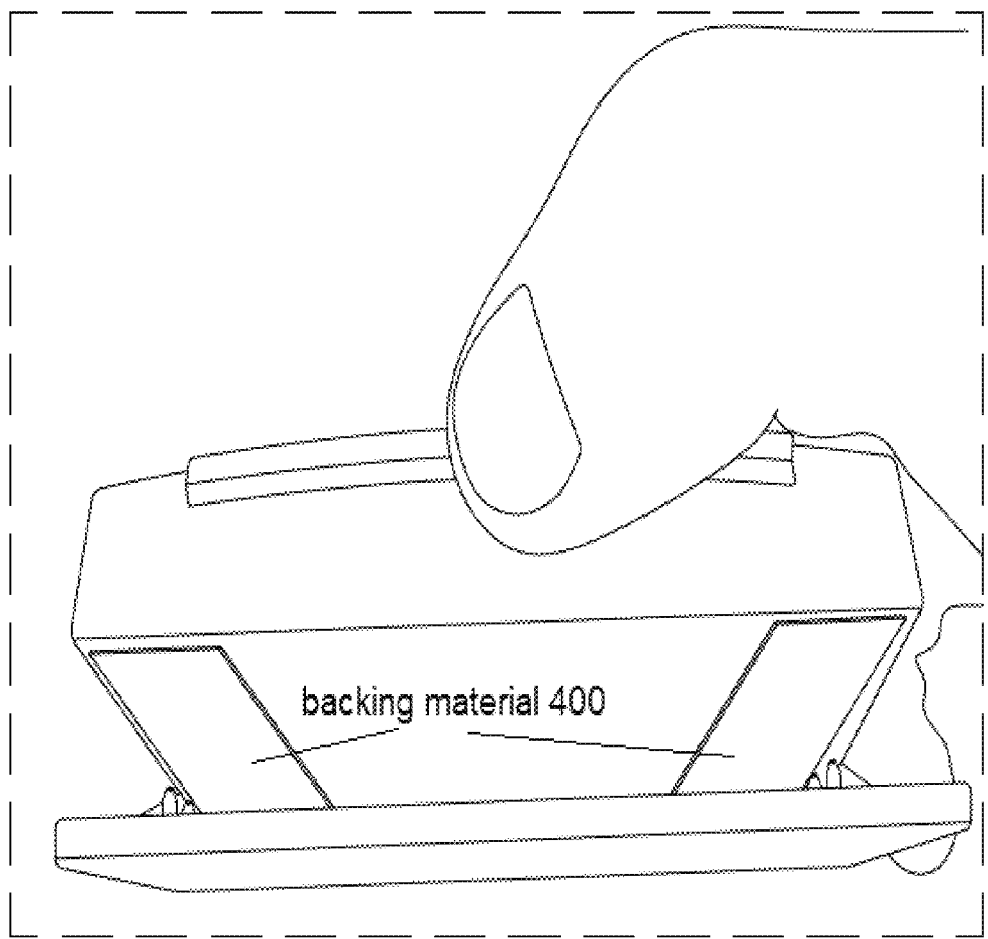
Figure 4E:
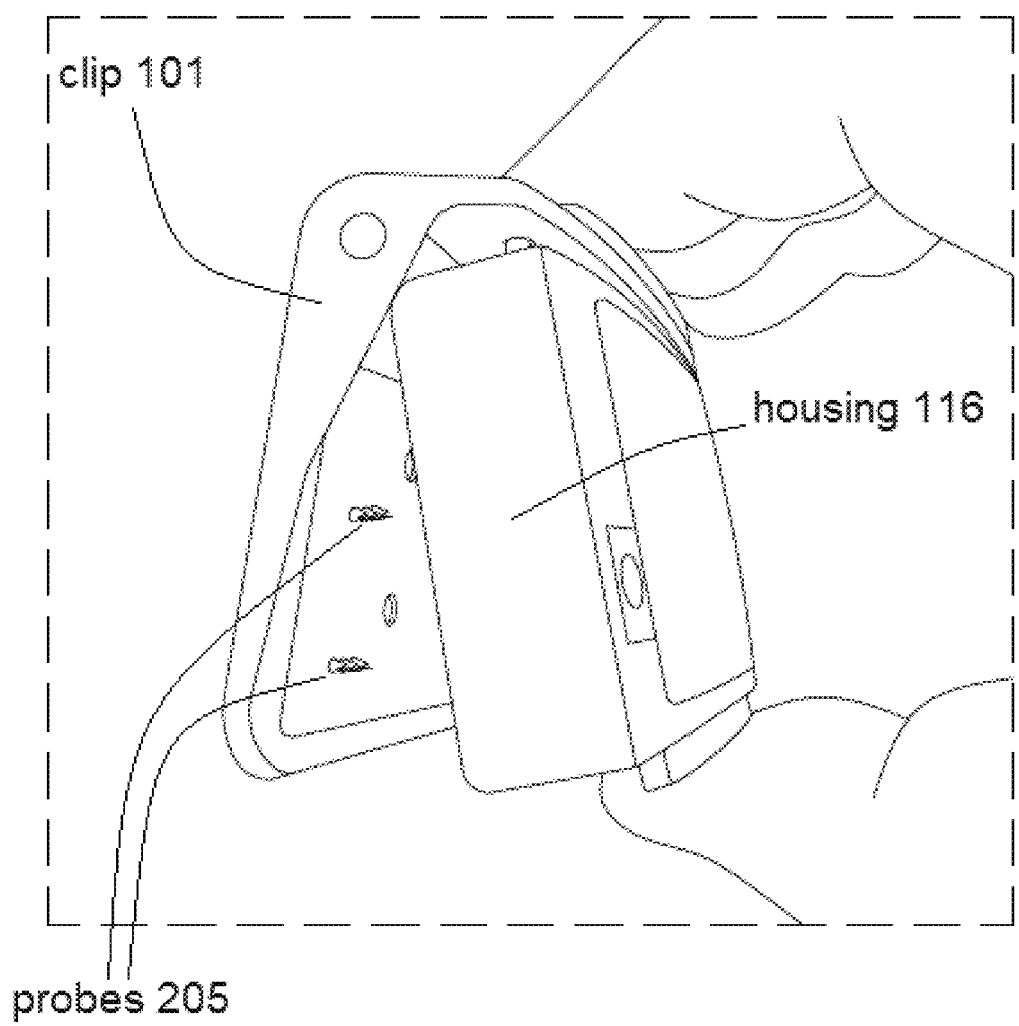

FIG. 3 shows a bottom view of the module 100. A top edge of the garment 510 takes an angled path 300 through the module 100, while the area of the garment 510 farther away from the edge 510 aligns along the direct (straight) path 301. The angled path 300 slightly tightens the top edge of the garment 510 and helps maintain correct orientation of the module 100 relative to the wearer's body. The structure 204 is angled to ease sliding the module 100 over the garment 510. The structure 204 also provides increased strength of the clip 101. The housing 116 is opened for attachment by squeezing the top of the clip 101 towards the housing 100.

FIGS. 4A-4E show the housing 116 in this opened position. The clip 101 is placed over the waistband, the probes 205 are then squeezed into the garment 510 and against the plastic backing 400 located on the back of the module housing 116. The backing strips 400 gives the probes 205 a firm but deformable surface to press into. This action serves to protect the sharpness of the probes 205 and to prevent damage to the housing 116.

In an embodiment, the module 100 makes connection to e.g. one or more electrodes 503 where two probes 205 clamp onto each electrode 503. However, as stated, other amounts of probes 205 and electrodes 503 can also be implemented herein. During use, a predetermined amount of current is passed through the two probes 205 and the voltage is measured between the probes 205. This voltage is used to determine if the probes 205 are both contacting the electrode 503. If both strips pass the test, an LED 105 will flash when the user presses the test button (switch) 104 (FIG. 1A). This attachment test is also performed during each measurement of moisture status. The attachment status is reported to the server. For the moisture measurement to be successful, only one probe 205 on each side needs to contact the electrodes 503. Therefore, a failed attachment test can still produce data, assuming one probe on each side is making contact.

Figure 5A:
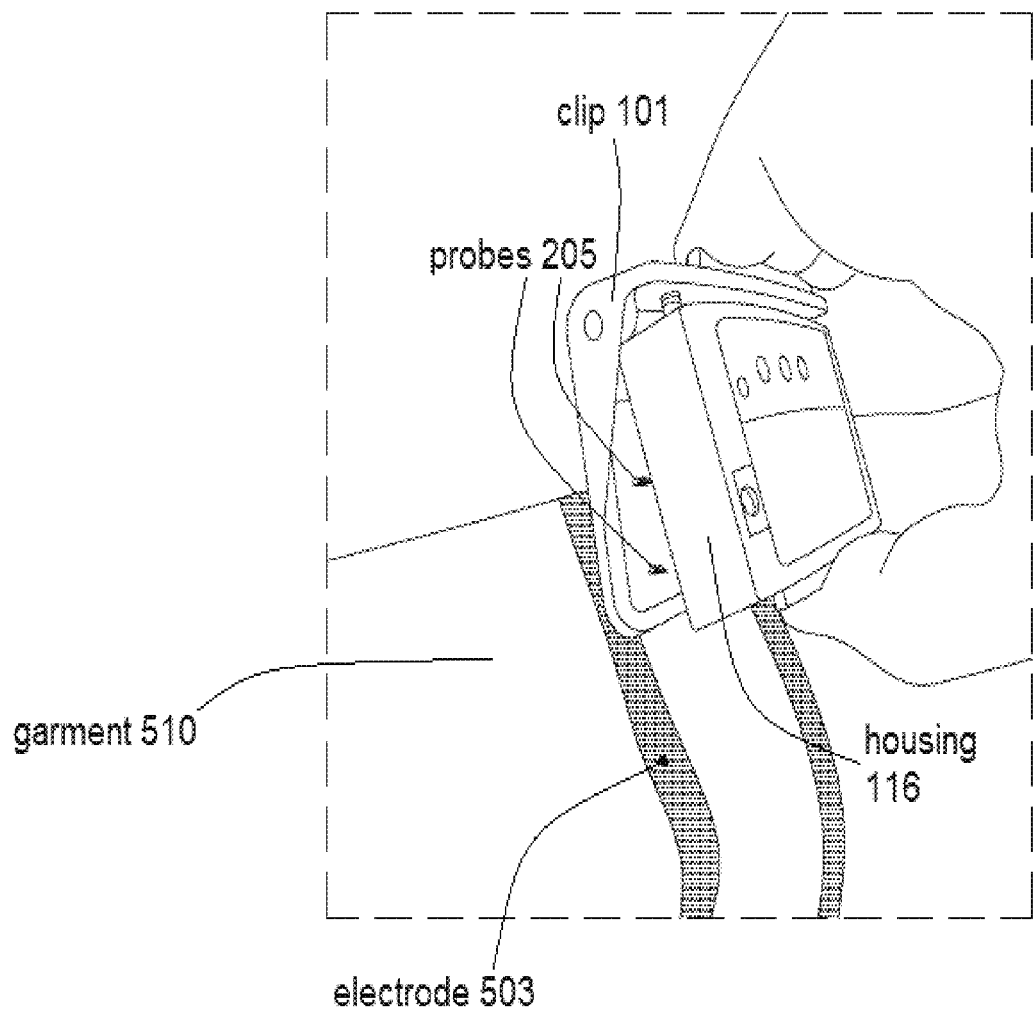
FIG. 5A shows the module in the process of attachment to a garment.
Figure 5B:
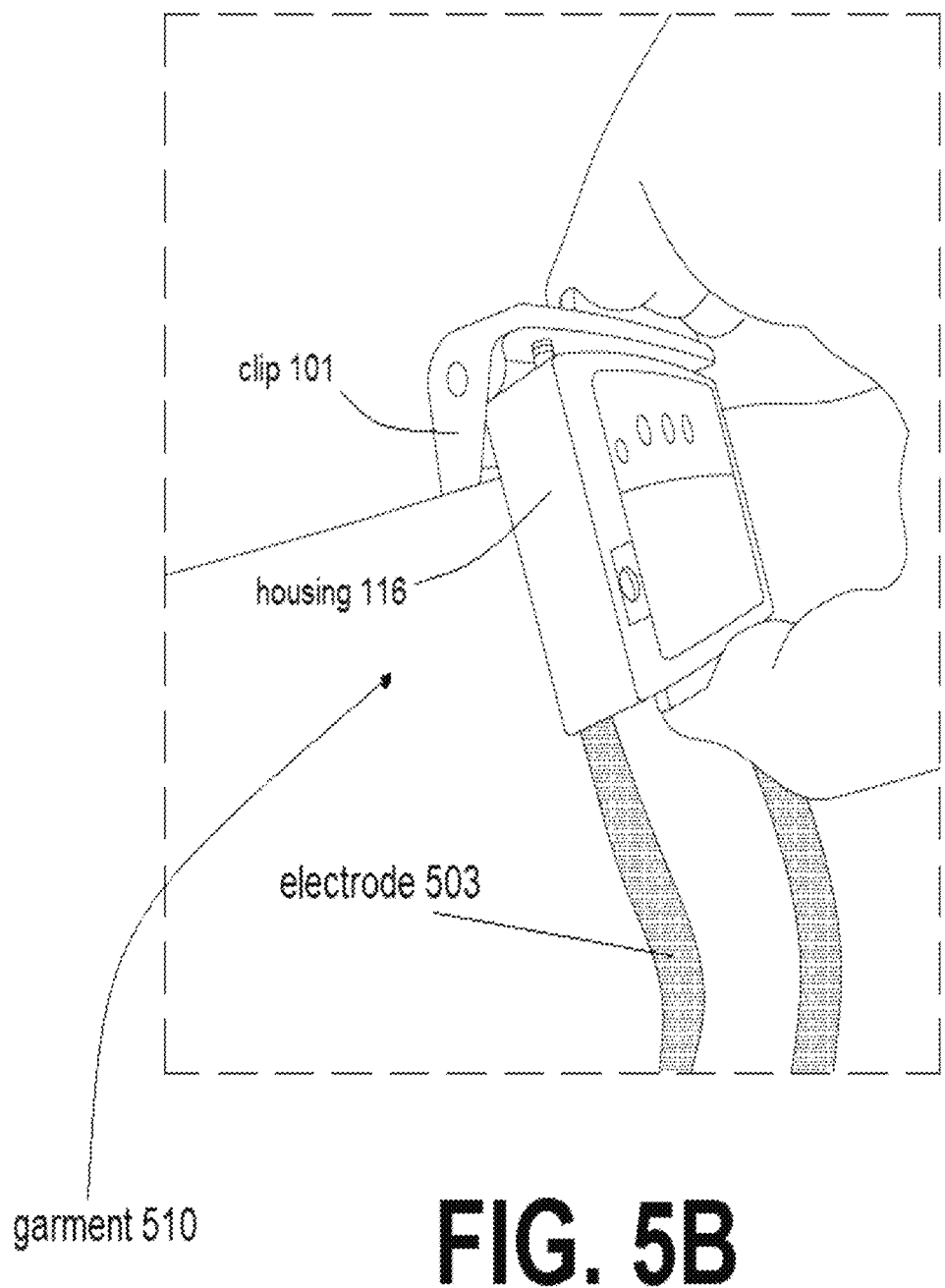
FIG. 5B shows how the module is attached\clipped to the garment.

FIG. 5A shows the module 100 in the process of attachment to a garment 510 having one or more electrodes 503 embedded or printed therein. From FIG. 5A it is apparent that the probes 205 (eventually) attach directly to the electrodes 503 (during use). The probes 205 penetrate one or more layers of material 504 in the garment 510 to contact the electrode 503. FIGS. 5A-5B show how the module 100 is attached\clipped to the garment 510. Meanwhile, FIGS. 5C, 5D, and 5E show cross section views of a probe 205 penetrating garment inner layers 504 over the conductive ink area. The differences between the FIGS. 5C, 5D, and 5E are mainly a taper within the tips 500-502 of the probe 205, and the resulting penetration of each. Specifically, FIG. 5C shows a highly tapered probe tip 500 piercing the electrode 503 and penetrating the backing disc 400. The backing disc 400 provides reliable material for probing, and is discussed in more detail with respect to FIG. 10A. In an embodiment, a suitable material 1008 for the backing discs 404 might be UHMW (Ultra High Molecular Weight) polyethylene. This piercing results in a low contact area between the probe tip 500 and the electrode 503 and therefor high contact resistance.

FIG. 5D shows a medium taper tip 501 contacting the electrode 503 with higher surface area and thus low contact resistance. This probe is an optimal design for the particular material used in the garment 510. The highly tapered tip 501 is also prone to wear, damage, and fabric snagging.

Finally, FIG. 5E shows a low taper tip 502 with incomplete penetration to the electrode 503. It this case excessive pressure is required to force the tip to the electrode 503. Again, FIG. 5C is shown merely for illustration and should not be considered limiting.

The specific composition of the probe 205 impacts contact reliability and durability. A non-oxidizing finish for the probe 205 such as gold is suitable, although tin may also be used. Silver plating for the probe 205 can also be advantageous because it is antibacterial, better conductor and less expensive than gold. The core material for the probe 205 impacts its durability. As such, steel, or other hard metal, maintains a sharp point longer than soft material such as copper.

As shown at least within FIG. 1, switches 104 are placed on the module housing 116 to allow a caregiver to press a switch for proper-attachment test (switch 104-T), urine incontinence (switch 104-1), or bowel incontinence (switch 104-2). In an embodiment, a press of the switch 104 also identifies the caregiver as being physically present with a patient (wearer) at the particular time. The meaning of pressing switch 1 or 2 is defined by predetermined computing resources (not shown). The attachment test switch (T) initiates a specific predetermined test sequence on the module 100.

Within the module 100, one sensor achieves void detection using the electrodes 503. Additional sensors can include but are not limited to an accelerometer and temperature sensor. Other embodiments comprise skin contact electrodes, IR temperature sensing, humidity, and gas sensor.

The accelerometer is used to indicate body position so that computing resources can determine how much time a patient has spent in a particular position. This information can be used to alert caregivers of potential conditions unhealthy for patient skin and thus prevent or reduce bedsores. Accelerometers can also be used for motion, a fall, respiration sensing, and general motion or activity.

As mentioned earlier, a temperature sensor 206 is located in the clip 101. The sensor 206 measures a surface temperature of a portion of the clip which is contact with skin. The temperature data is useful to determine body temperature and confirm proper placement of the module on body. Similarly, an infrared (IR) sensor can be used to measure skin temperature. However, other mechanisms can also be used. Temperature is an important consideration of the embodiments herein.

The clip portion of the housing 116 has access to the skin which is needed for IR sensing. Conductive contacts on the clip 101 can be used to measure skin resistance, or verify module position against the skin. Additionally, capacitive sensing elements could also be placed in the clip 101 for the purpose of sensing housing position.

Indicators

The module housing can include user interface features such as an LED, beeper, tactile switches, and alignment labels. However, for clarity, only the LED 105 and tactile switches (AKA buttons) 104 are shown in FIG. 1A. In an embodiment, a beeper (not shown) helps confirm the attachment test and switch presses, especially for users with limited technical proficiency such as those employed in nursing home. Labeling provides a visual aid and reminder to align the module housing 116 with the ink strips when attaching. As shown in FIGS. 5A-5B, the electrodes 503 are visible from the outside of the garment 510.

The embodiments herein further comprise a single LED that blinks to indicate a status of the module 100. Other display options are possible and include LCDs, electronic paper (E-paper), multi-color LED, or sound emitters. In an embodiment, a display that can indicate a status of a garment could also be located in or near the patient's room so that status is seen at a glance.

Advertisement

A Bluetooth advertisement is a short radio transmission intended to notify listening devices (typically phones, computers <sometimes acting as an access point>, and tablets) that a Bluetooth device is present. Advertisements are the first step in establishing a connection. Advertisements contain Bluetooth standards-defined data and a small amount space for user data. In environments using the garment system 180 (usage-context) e.g. FIGS. 1B-1C, the advertisements are used to send the sensor and status data from the module 100 to a larger computer network and patient database. This is not typical for Bluetooth applications but does solve an underlying issue with Bluetooth devices. That issue is pairing.

Pairing is the connection approval between a Bluetooth device and other device such as a mobile phone or access point. Bluetooth pairing gets increasingly unreliable as the complexity of the wireless environment increases. The embodiments herein serve large-scale environments, in which there are many caregivers and many patients (wearers of the module 100). As such, the burden of maintaining a properly configured paired Bluetooth connection is substantial. Accordingly, for the scenarios described herein, a non-paired method is normally used.

However, the module 100 and system 180 described herein is capable of other Bluetooth connection modes including extended advertisements and paired operation. In order to extend battery life, these modes are normally not used. However, these modes can be enabled for special conditions such as initial field setup, manufacture testing, field testing, or special data collection.

The power required to send a Bluetooth advertisement is low and thus the advertisement-only mode provides low power consumption. The electrical energy needed to listen for advertisements is comparably high because the receiver circuit consumes significant energy and must be constantly active. To address this, the embodiments herein use wall-powered access points 152 or devices with high-capacity batteries to listen for the periodic Bluetooth advertisements from the modules 100, as shown in FIGS. 1B and 1C. Other changes include modifying the battery terminals to eliminate shorting, and a front side connector for programming while in use. Further, it is possible to use the battery door to help position the batteries within the housing.

Battery Life

The following are various non-limiting steps or features for extending a battery life for the module 100.

Typically, the module 100 "sleeps" almost all of the time. Even sending data every 15 seconds is accomplished in a matter of milliseconds and then "sleeps" for the balance of the 15 second period, unless one of the buttons (switches) 104 on the module 100 is pushed.

The module 100 can include additional changes to the activity during the "sleep mode" to even further reduce power usage. An amount of current consumed during sleep can be reduced by another ½ to ⅔, thereby further extending battery life. In an embodiment, the LED light can flash rather than stay on solid, reducing power usage.

The embodiments herein also provide a low battery indicator. This indicator should somehow indicate both potential problems: voltage used and time in service. To facilitate this, some type of clock mechanism can be incorporated into the module 100.

A battery change protocol can be managed in a computer-implemented protocol, perhaps to be solved at the server or cloud level, or level of the system 180. It could be incorporated into a mechanism that registers a module 100 to a specific patient and provide an alert to management through the system 180. This would be in contrast to or conjunction with a light on the housing 116, e.g. the LED indicator 105.

Bluetooth paired mode and Near Field Communication (NFC) modes are potentially useful for setup or special use-case applications. The access point 152 includes hardware to support (occasionally) paired Bluetooth operation. Further, many mobile phones now include NFC capability as standard equipment, and along these lines, NFC could be added to the access points 152. Additionally, the repeaters 601 are also capable of Bluetooth advertisement only, Bluetooth paired, and NFC modes.

Wireless Topology

Because of walls, wiring furniture, equipment, Bluetooth radio range is limited and is typically less than 100 m, even with no obstacles. The indoor range is less and may be insufficient for a centralized receiving device to detect all modules in a typical nursing home or residential facility. To overcome this, the system 100 uses the access points 152 distributed throughout the facility to receive Bluetooth advertisements, and then relay the data to a central server 128 using other wired or wireless networks. A mesh or cluster topology could be applied to the access points 152, WiFi points, or to any device used as part of the system 100. This topology could include but is not limited to display terminals, status indicators, smart phones, or modules 100.

Setting aside pairing, another approach to this range issue is Bluetooth advisement repeaters. In this approach, Bluetooth advertisements are repeated by transceivers for the purpose of extending range. Eventually an end point device will receive the Bluetooth advertisement for the purpose of displaying data, alerting, or making the data available to another system such as a centralized server. A specialized wireless repeater that facilitates only Bluetooth advertisements, that is, a Bluetooth-only repeater is contemplated.

Bluetooth is the primary communications standard used although near field communication (NFC) and Long-Range (LoRa) network standard may be used. NFC is very short range (inches) and would be mostly used for configuration, testing, program updates, or data transfer purposes. LoRa could provide a means to transmit from module to a server or access point located at a distance much farther than Bluetooth. An embodiment uses a standard advertising packet to broadcast data from the modules 100 to the access points 152. This comprises a single packet, with all data contained in that single packet. This packet may be repeated, but the packets are all identical. One advantage of such standard (legacy) advertisements is compatibility across all versions of the system 180 and module 100.

An embodiment will transmit more data than can fit in a legacy (e.g. V4.0) BlueTooth packet and will need to transition to an updated single advertisement packet (e.g. V4.2, 255 bytes), or extended advertisement (e.g. V5.0, 1650 bytes) or to a connected mode (paired, unlimited). Bluetooth's paired mode operation may sometimes be used. Doing so would limit the roaming ability of the modules among multiple access points so pairing may be a temporary mode.

BlueTooth has a variety of advertisement modes. Bluetooth has expanded its advertisement capability over time. At one time, Bluetooth contained 3 broadcast channels, but then expanded to as much as 37 broadcast channels. A similar expansion occurred in which a Bluetooth packet had at one time a maximum capacity of 37 bytes, but then expanded to as much as to 255 bytes of data per packet. The embodiments herein take advantage of this, sending more data per packet and thus transmitting the packets less frequently. This in turn means that the module 100 can add more sensing capability and features.

Figure 6:
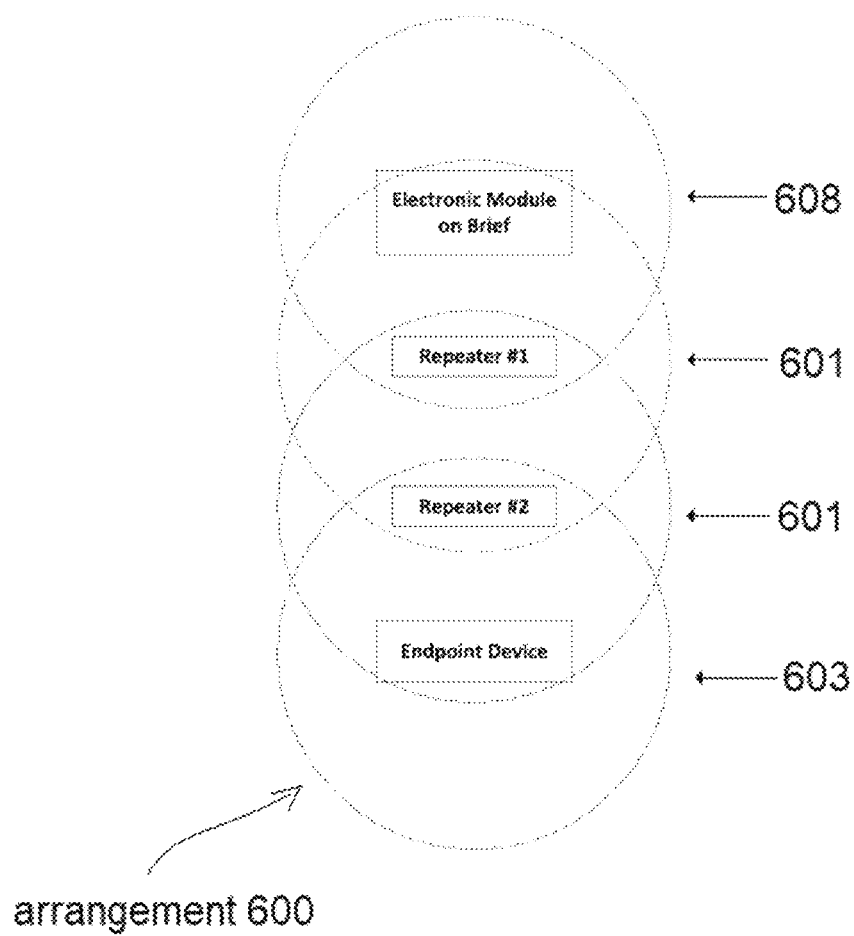
FIG. 6 shows an arrangement comprising a module, two repeaters, and one endpoint device.

FIG. 6 shows an arrangement 600 comprising a module 100, two repeaters 601, and one endpoint device 603. The circles 600, 601, and 603 show the transmission range of each device respectively. The devices in this example are arranged so that the electronic module's transmission can only reach repeater #1 as illustrated by circle 600. The transmission range of repeater #1 shown as 601 can reach repeater #2 and the electronic module. The transmission range of repeater #2 shown as 602 can reach repeater #1 and the endpoint device. Finally, the transmission range of the endpoint device shown as 603 can only reach repeater #2. This arrangement shows how a transmission from the electronic module can be repeated to extend range. FIG. 6 also conveys that depending on the placement of the endpoint device and transmission range, a particular device may reach a number of other endpoint devices.

A mechanism must be employed to prevent repeaters 601 from continually repeating the transmissions of each other's data. Otherwise, the repeater 601 could pass the same data back and forth endlessly. There are many possibilities to prevent this situation. However, the embodiments herein do rely on particular repeater placement locations or repeater uniqueness. This preserves the ability to randomly place repeaters without concern for ranges of particular devices or their ID. The goal of the repeaters 601 is to provide continuous and extended range from a module 100 to endpoint device 603. Modules 100 and endpoints 603 are likely mobile and the repeating function can be part of mobile devices. Therefore, the network of repeaters is not fixed or limited to just what is shown herein, as these drawings are for illustration-only and are not limiting.

Figure 7:
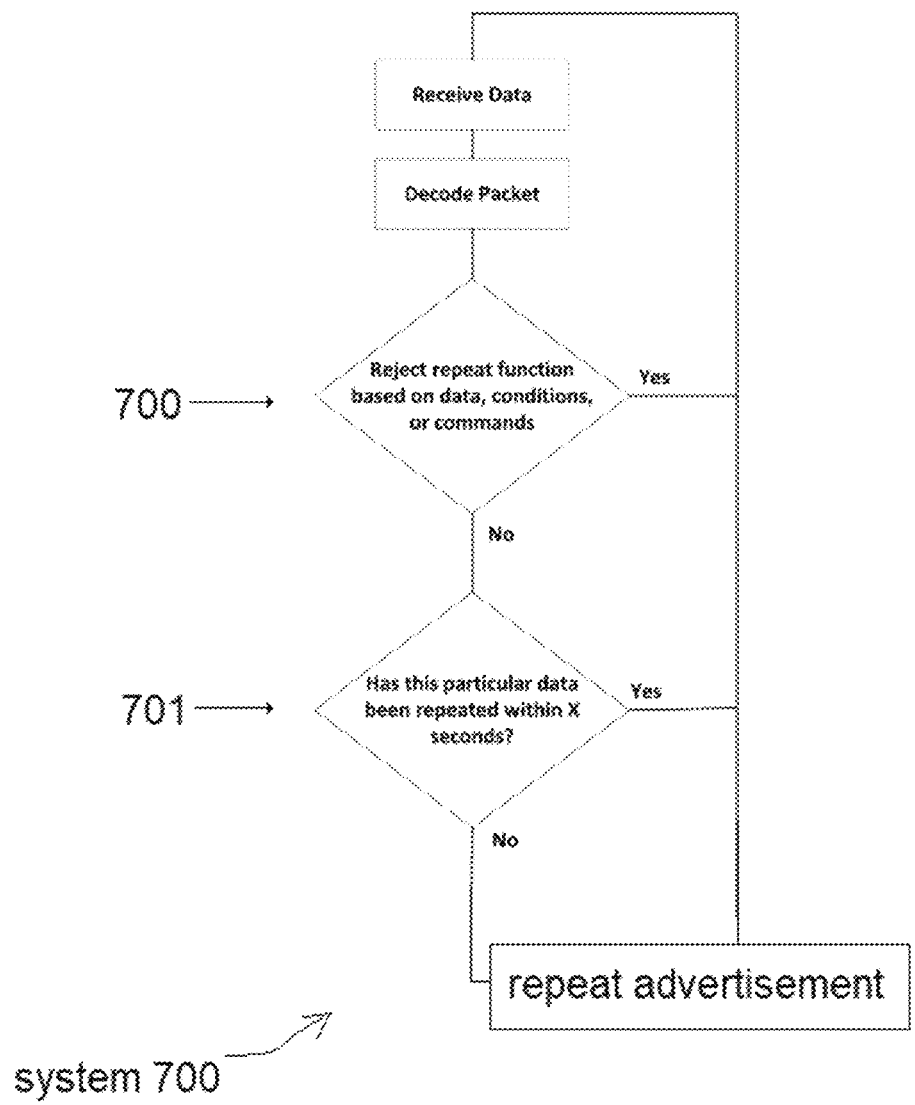
FIG. 7 shows an example method to prevent unwanted repetition of advertisements.

An example method 700 to prevent unwanted repetition of advertisements is show in FIG. 7. The repeater 601 scans constantly for an advertisement and then decodes an advertisement packet. A decision to repeat the advertisement, or not repeat, depends on several factors.

A first step 704 is testing for commands or data the control repeating and the second step 708 is a determining if the advertisement has already been repeated. Examples for step 704 would be reject all non-advertising packets. Example for step 708 is reject a packet if it has been repeated within the last 15 seconds within the system 700.

Many parameters can use used to control the repeat or reject function. Some of these are:

MAC address in packet Each Bluetooth device and hence module 100 typically has a unique MAC address. That can be used to provide a selective filter to allow only data from particular modules to be repeated.

Company ID—A company ID is included in the packet. That can be used to for selection.

Group ID or Whitelist/blacklists—Groups formed from ID data, MAC data, or combinations of identifiable data enables rejecting or accepting by group.

Sensor data—Sensor data can be used for rejecting, or accepting,

Origin of data (first repeat hop) a path taken by the advertisement can be included.

RSSI (signal intensity). Low RSSI signals can be rejected to prevent excessive repeating BT traffic. Repeaters can be skipped during times of excessive advertisements packets being broadcast. This can prevent repeaters from adding too much traffic.

User selected control—A user may be able to identify a particular device to the repeater for accept or reject.

Type of repeater—Repeaters may be battery powered or 120V powered and may include particular features. Depending on the repeater type, the repeat function may be managed to conserve power, or prioritize other features.

Remaining battery charge of repeater (assuming portable), if a repeater 601 is running low on battery.

Command present in packet—A command generated by the system can be included the packet to control the repeating function.

Data in packet in comparison to previously received data—Data redundancy checks can be performed to reject repeats.

Commands sent via a special command advertisement by module or other device—A packet may consist of control only and be intended for particular repeaters. For example, repeaters with RSSI of a particular level may be commanded to indicate reception.

In addition to the parameters above, the use of time delays and idempotency tokens can be used to prevent repeaters from unwanted repeating. Time delays act as a test whether enough time has passed for a particular advertisement to have fully propagated through the repeater network. Meanwhile, an idempotency token uniquely identifies an advertisement to prevent unwanted repeated. Idempotency tokens may be generated either by the module 100 or the repeater(s) 601. In addition to repeating advertisements, the repeaters 601 can be instructed to pair and to unpair with devices for establishing two-way communications for the transfer of data.

Figure 8:
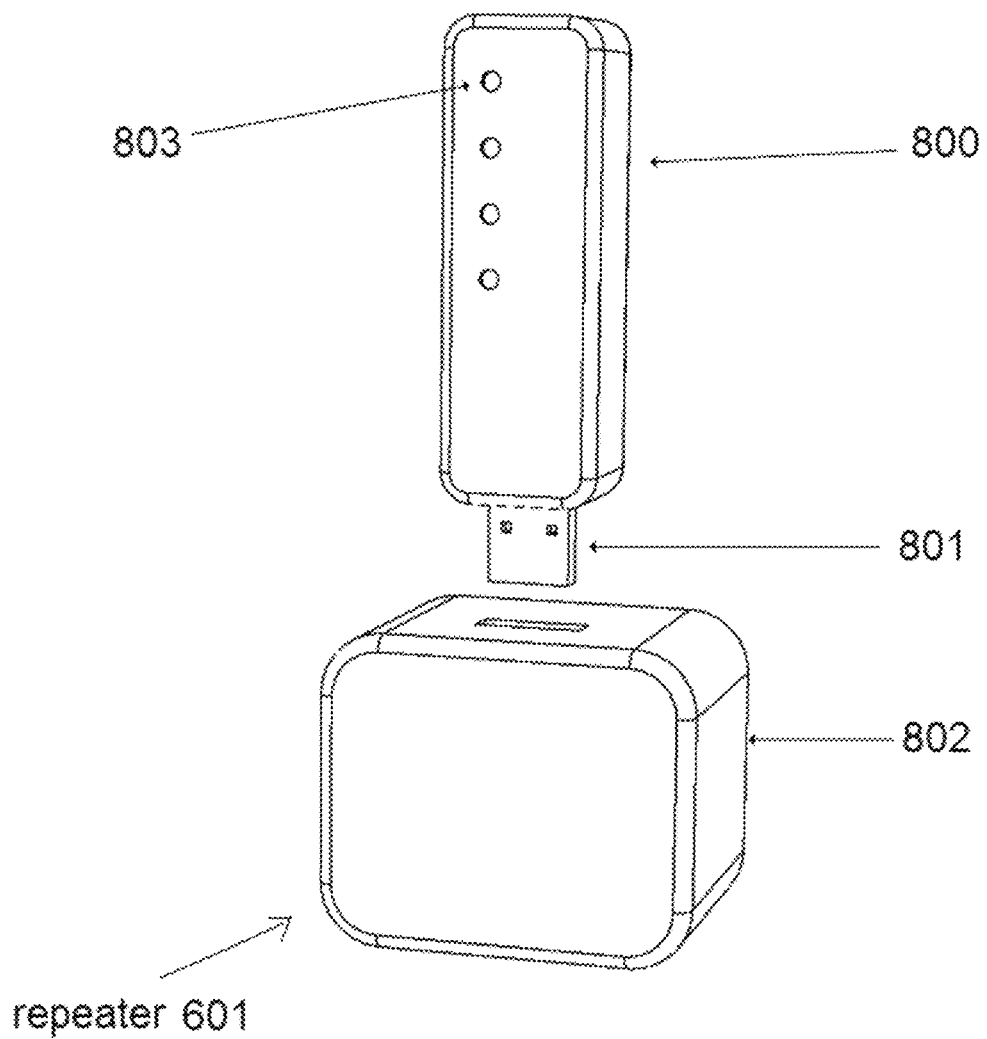
FIG. 8 shows a perspective view of a repeater using a USB drive enclosure with a USB mechanism plugged into a USB power supply.

FIG. 8 shows a perspective view of a repeater 601 using a USB drive enclosure 800 with USB plug 801 to be plugged into a USB power supply 802. One embodiment of the repeater is a USB thumb drive size device that plugs into a USB power source such as a USB charging supply. Four status LEDs are show indicated by the top LED 803. The status LEDs can be programmed to indicate data from advertisement, power, or wireless connection status.

The repeater 601 can also include a secondary purpose such as a nightlight, thermometer, lamp, or clock. Data from a packet can be used to control a feature of those devices. For example, a wetness indication could change the nightlight color to provide a simple visual indicator. Endpoint devices primarily serve to display status data but may include alert features such as a beeper or vibration feature. The endpoint devices can also provide the repeating function for other modules or endpoint devices.

A repeater 601 can include features such as memory, real time clock and calendar, time stamping functions, external network interface such as Ethernet or WiFi, removable memory, or smart home device interfaces such as Amazon echo. The purpose of these functions is collection of data and remote or automated management.

A network of repeaters 601 can also be used for advertisements other that the electronic brief module. For example, data for non-patient use include door or lock status, appliance status, temperature, humidity, doorbells, mailboxes, call buttons, medication reminders, etc.

Figure 9:
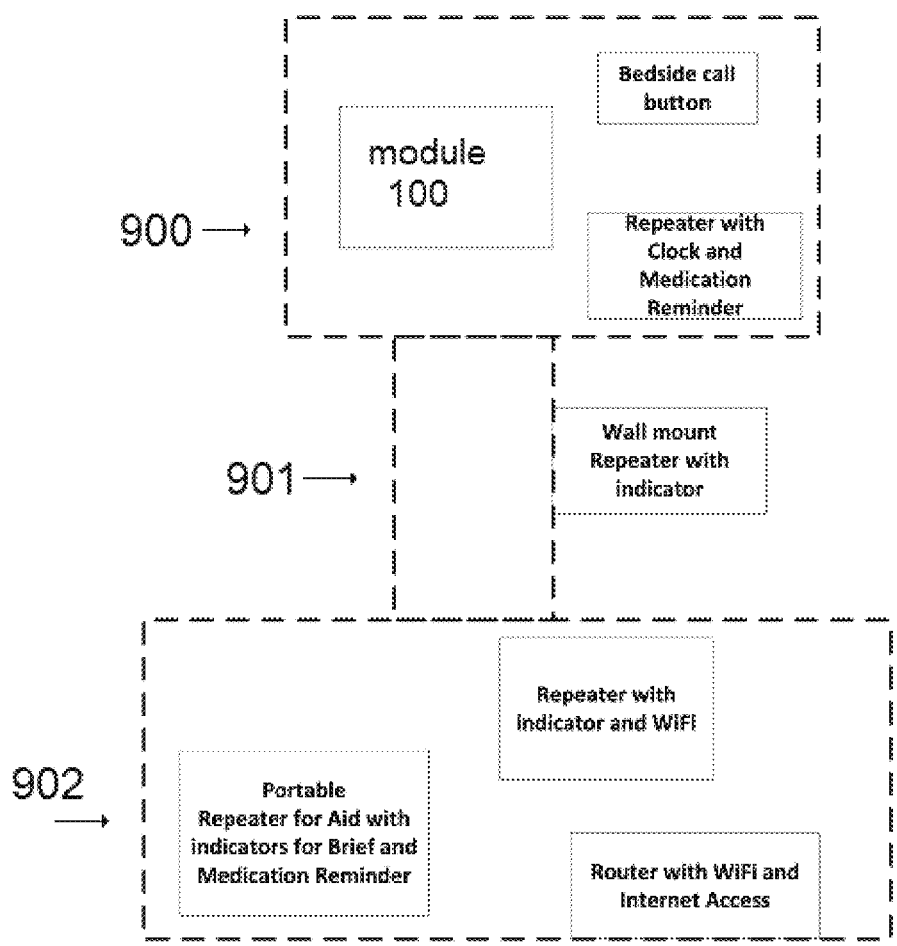
FIG. 9 shows an embodiment where a patient's room includes a bedside call button and repeater with clock and medication reminder.

FIG. 9 shows an embodiment where a patient's room 900 includes a bedside call button and repeater with clock and medication reminder indicator. This would allow a caregiver to see a status of a module 100 at a glance while anywhere in the room 900. A repeater located in a hallway 901 contains a wall-mounted repeater 601 as shown in FIG. 8. The living room 902 contains a repeater 601 with WiFi access via a router. A portable repeater with indicators is also shown in this room. The module 100 and portable repeater for the air can be moved without impacting wireless coverage.

A test mode to check the status of a repeater 601 may be included. This is a specialized advertisement designed to command the repeater 601 to measure receive signal strength of each repeater for each advertisement source. An advertisement source can be a module 100 or other repeaters. Such a test mode is useful in optimizing placement of the repeaters 601 to prevent poor coverage areas or excessive coverage overlap.

Figure 14:
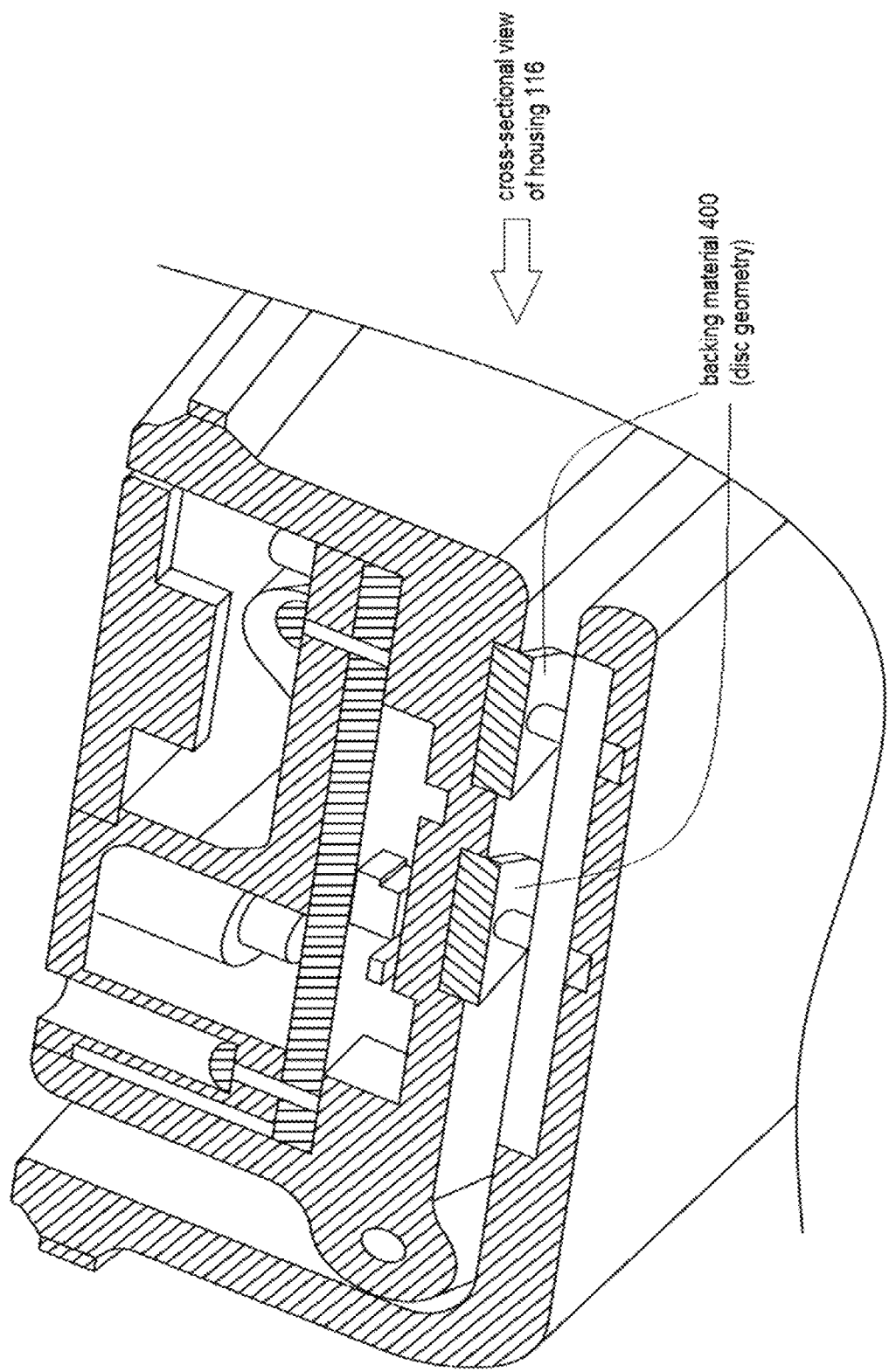
FIG. 14 shows an example where the backing elements in the form of strips, molded shapes, or deposited materials on the module body.

FIG. 14 shows an example housing 116 where the backing elements 400 (e.g. discs) could be replaced by strips, molded shapes, or deposited materials on the body of the module 100. Further, the backing material 400 could be made replaceable to accommodate wear or different brief materials. Within FIG. 14, the probes 205 are shown contacting neoprene discs bonded into shallow pockets of the housing 116. In FIG. 14, the backing elements 400 are shown having a disc-like geometry, but this specific geometry is not to be considered limiting, and is for illustration-only.

Additionally, these backing elements 400 could, in an embodiment, be replaceable items. In an embodiment, the probes 205 press through the garment 510 and then push into a backing material 400 (in an embodiment, a neoprene disc). As discussed earlier, the backing material 400 protects the tips of the probe 205 and increase the surface area of the connection by allowing the brief to bend slightly at the point of contact. Grip and durability of the contacts is also improved using the soft neoprene backing material.

Configuring/Assigning Modules to Patients

Configuration of modules, patient-assignments, and settings of the system 180 (FIG. 1B) is a recurring cost of using the embodiments herein. For the system 180 described herein to work well and be advantageous in a residential facility, these tasks must be smooth and seamless. Managing patient and caregiver linking, settings, and other data inputs may benefit from Radio Frequency IDentification (RFID) tags, NFC devices, bar/matrix/QR codes, and Bluetooth or LoRa communications. The labor saving and accuracy of using these options over manual entry could be significant.

Accordingly, for the task of assigning a new module to a patient and or caregiver, in an embodiment, each patient has a RFID tag loaded with patient ID number, each caregiver has a RFID tag with patient ID number, and any specific module 100 can be equipped with NFC reader. One way to assign a specific module to a patient would be to hold a patient tag near to the module 100, and press a "read" button on the module 100. Doing so would combine patient ID with module ID and send an update to a server.

Similarly, to assign a module 100 to a caregiver, hold a caregiver tag near to the module 100, and press the "read" button on module 100. This combines caregiver ID with module ID and uploads to a server. Meanwhile, to remove a module from the system, hold a RFID tag loaded with a "remove" command near to the module 100, and press the "read" button. Doing so would combine a "remove" command with the module ID, and uploads this task to the server.

A specific separate caregiver device for viewing status, assign modules, and configuring such as but not limited to what is described above could be included as part of the embodiments herein. This could serve as a substitute for adjunct with pagers and/or smart phones.

Machine Learning

Machine learning can be used to establish immediate care threshold levels, create forecasting of void events, and identify potential health issues. Data from a void sensor in a module 100, temperature sensors, position sensors, elapsed time, time of day, and other parameters may be used to build a probability model of both the present and near future void status. This may be useful in determining brief change urgency, planning activities, and scheduling care. Machine learning can also be used to reduce broadcast storms, un-necessary and redundant alerts, and improved data management and targeting of alerts to be more relevant.

Manufacturing and Assembly

The above discussion was focused on the features and functionality of the module 100. What follows will be a discussion of manufacturing, assembly, and testing of the module 100. Specifically, the following overview shows some potential tasks and sub-tasks necessary to properly assemble an example module 100. The order of the following tasks can be changed as needed. Their description is merely for example only, and thus should not be considered limiting.

Punch neoprene discs 400
Cut hinge rod 200 to specific predetermined length and finish ends
Perform various battery clip modifications
Clean holes for the hinge rod 200 in housing 116 and clip 101
Set threaded brass inserts in main housing
Bond neoprene discs 400 to main housing 116
Trim probe tips from spring probes
Solder probe tips and flex cable to probe PCB
Probe board bonding to clip 101
Initial power test and programming main PCB board 202
Module housing assembly
Main PCB board 202 install
Functional testing
Heat stake hinge rod 200

As stated, there can be many different sequences of assembly and testing, and the below 16 steps (generally) can occur in a variety of orders. Thus, the following 16 steps are for illustration, clarity, comprehensiveness, and enablement, but should not be considered limiting.

1) Punch Neoprene Discs

Figure 10A:
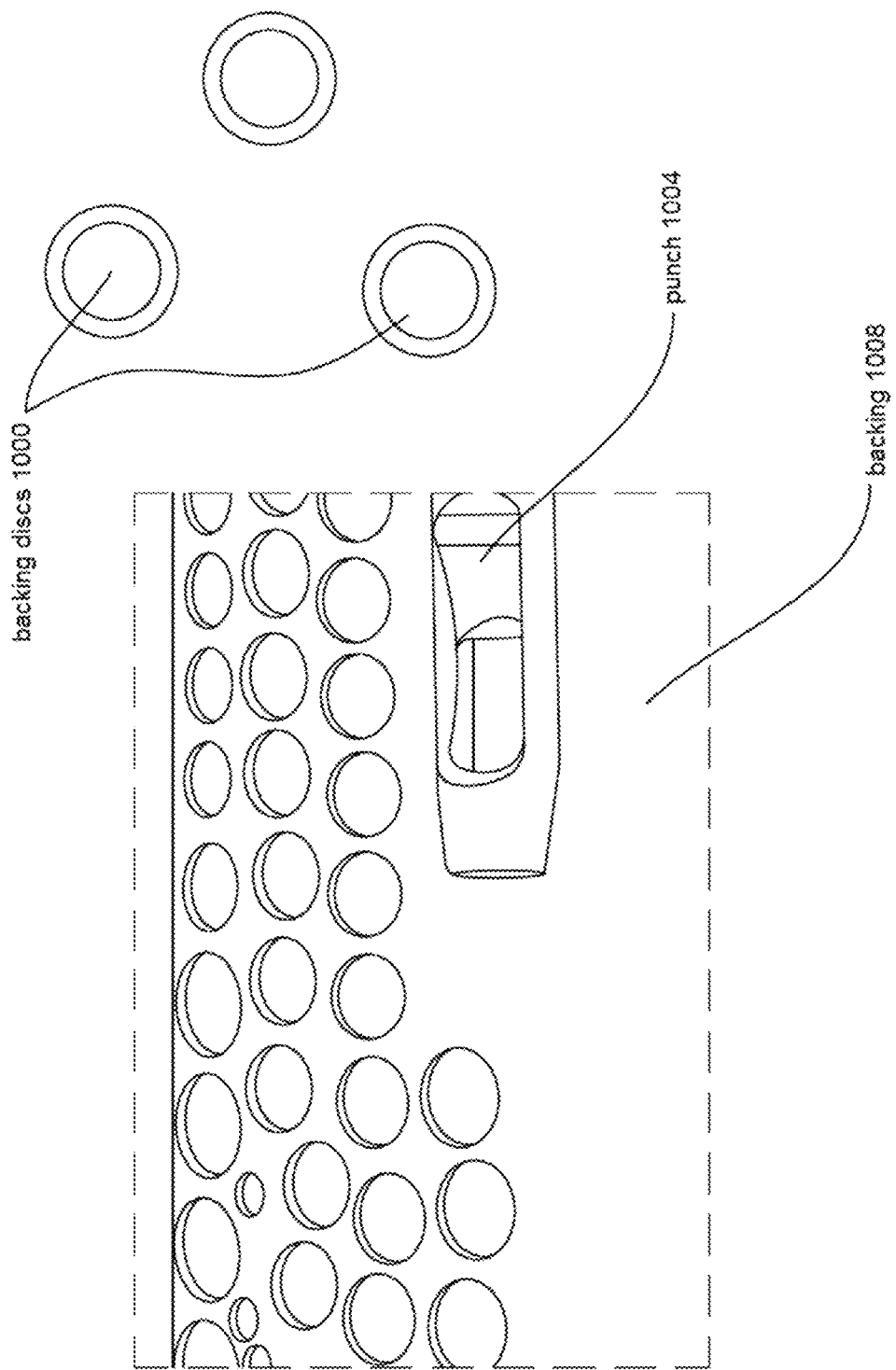
FIG. 10A shows neoprene backing discs being punched from a sheet of backing material.

As shown in FIG. 10A, neoprene backing discs 400 for the probes 205 can be punched from e.g. smooth 1/16" thick sheet 1008 comprising the backing material 400. In an embodiment, it is possible to use a McMaster PN 1370N13 as material for the backing material 400. For the punch 1004 it is possible to use a 3/8" hollow punch.

In performing the punch-task, it is best to hold the punch perpendicular to the sheet to obtain a crisp 90-degree edge. Then, punch against flat solid material like hardwood or hard plastic. A single medium-strength hit should cleanly punch the disk so as to be well-formed.

2) Cut the Hinge Rods 200 to Length and Finish Ends

In an embodiment, the hinge rod 200 is supplied in long straight lengths. One optimum diameter for the hinge rod 200 is 1/16". It is helpful to avoid bending the rod 200 because bends can make installation difficult. Cut the hinge rods 200 to e.g. ~90 mm lengths. Sawing is helpful to producing a clean cut. Side cutters can also be effective.

Sand one end of the hinge rod 200 flat using a stationary belt, disc, or grinder. Use fine sandpaper or file to deburr any remaining edges if needed. Sand the opposite end flat to get a rod length of e.g. 87.5 mm, although this may change depending on the dimensions of the housing 116. Taper one end of the hinge rod 200 as shown to aid in installation later.

3) Battery Clip Modification

The battery clips 1220 can be modified by trimming the battery holding portion. Compound action (Wiss type) snips are suitable to snip-cut the metal with minimal effort and distortion.

4) Cleaning Hinge Rod Holes in Housing 116 and Clip 101

The housing 116 can be manufactured by any of 3D printing, extrusion molding, injection molding, or other method. Regardless of the specific method, after manufacture of the housing 116, the holes for the hinge rod 200 are sometimes still not clean enough to insert the hinge rod 200 during assembly. It is important the installation of the hinge rod 200 be trouble free, since the hinge rod 200 is installed while the module assembly is held under spring pressure.

To address this, it is possible to use a drill bit to clean the hole 203 for the hinge rod 200. In an embodiment, an extended 1/16" drill bit (e.g. McMaster PN 29315A116) can be used. The drill bit will need to be inserted from each end of the housing 116 since the bit is not long enough to pass thru both at the same time.

Next, an assembler should test-fit a hinge rod 200 to verify the hole 203 is clear. The hinge rod 200 should be snug but not lose as to fall out of the housing 116. The amount the holes 203 needs to be cleared will vary slightly depending on the manufacturing process. It is best to drill slowly to avoid melting any plastic. Further, it may be suitable to pull the bit out occasionally to clear material and prevent melting.

Occasionally plastic can be difficult to drill precisely, since some plastics may prefer to compress rather than be cleanly cut by a drill bit. The result is a hole slightly smaller than the drill bit used to drill the hole. If the hinge rod holes 203 require significant removal of material, the resulting hole from the 1/16" bit may be slightly smaller than 1/16". This makes the hinge rod 200 difficult to install. To address this, a slightly larger bit such as a #52 or #51 can be used to clear enough plastic. It is important to get both sides of the hole 203 aligned on axis so that the hinge rod 200 properly passes though both sides in a co-linear fashion. Extended length drill bits help with alignment by bridging the two sides.

5) Brass Thread Inserts

The following process can be used to manually install a plurality of brass thread inserts, potentially without using any special equipment. The brass inserts are pressed partially to depth and then heated to sink them to a flush final depth. The brass inserts should be installed to be flush with the surface of the housing 116 and not below the surface.

A manufacturer will hold the insert during pressing using a specially-designed tool. Keep tool perpendicular to the housing 116 during pressing.

A soldering iron can be used to set the inserts to be flush. Further, it is possible to achieve a flush-effect using an insert with excess plastic trimmed if required.

6) Bond Neoprene Discs to Main Housing

The discs 400 are glued into indentations on the back side of the main housing 116. In an embodiment, 3M DP105 adhesive can be used, although the embodiments herein should not be considered as limited thereto. Some adhesives have a short working time. Thus, timing is important. That is, it is important not to use any adhesive if it is already beginning to thicken as it will not bond as well.

Clean the neoprene discs 400 to remove any oil. Then, apply a dot of adhesive to disc indentations. Do not overapply the adhesive, as it is advantageous to prevent any adhesive from seeping out. Place the discs 400, press gently, and cover using paper. In an embodiment, use a small weight to hold in place.

Avoid attempting to wipe excess adhesive if it seeps out from the edge of the disc. It is easier to allow it to cure, and then trim it away with a fresh razor blade.

7) Trim Probe Tips from Spring Probes

Tips for pogo probes are used as contact probes 205. These tips can be cut using a handheld hard wire cutter. A simple fixture is used to position the probe 205 so that the tip 500\501\502 will be at a suitable length. If this is done properly, no additional steps to trim the length should be required. Next, rest the probe 205 in the plastic block. Then, cut the probe tip 500\501\502. The metal stop strip is intended to flex during cutting to protect the probe tips 500\501\502.

8) Solder Probe Tips to PCB

The probe tips 500\501\502 are easily damaged. Accordingly, it is recommended to avoid stacking finished boards where the tips 500\501\502 may contact other boards. To achieve this, place a second bare board over the probes 205 to hold them in place. Flip the board stack, hold in place with a weight and then solder the probes 205. Use extra dwell time to heat the pin and also achieve good solder flow. Avoid over-soldering so as to prevent any solder flow onto the tip side.

9) Solder Flex Cable to Probe PCB

Next, a manufacturer will solder the flex cable 1050 to the probe board. Hot bar soldering would be ideal; however, hand soldering can also be suitable.

10) PCB Assembly Notes

Solder the battery terminals shown from bottom side. A little extra dwell time on the connection before applying solder helps with wetting of the plated metal. The trimmed battery terminals can be held in place using a wood block. The housing 116 should then be flipped over and a weight used to hold the PCB 202 flat against the battery terminals 1220 during hand soldering.

11) Bonding Probe Board to Clip

Figure 10B:
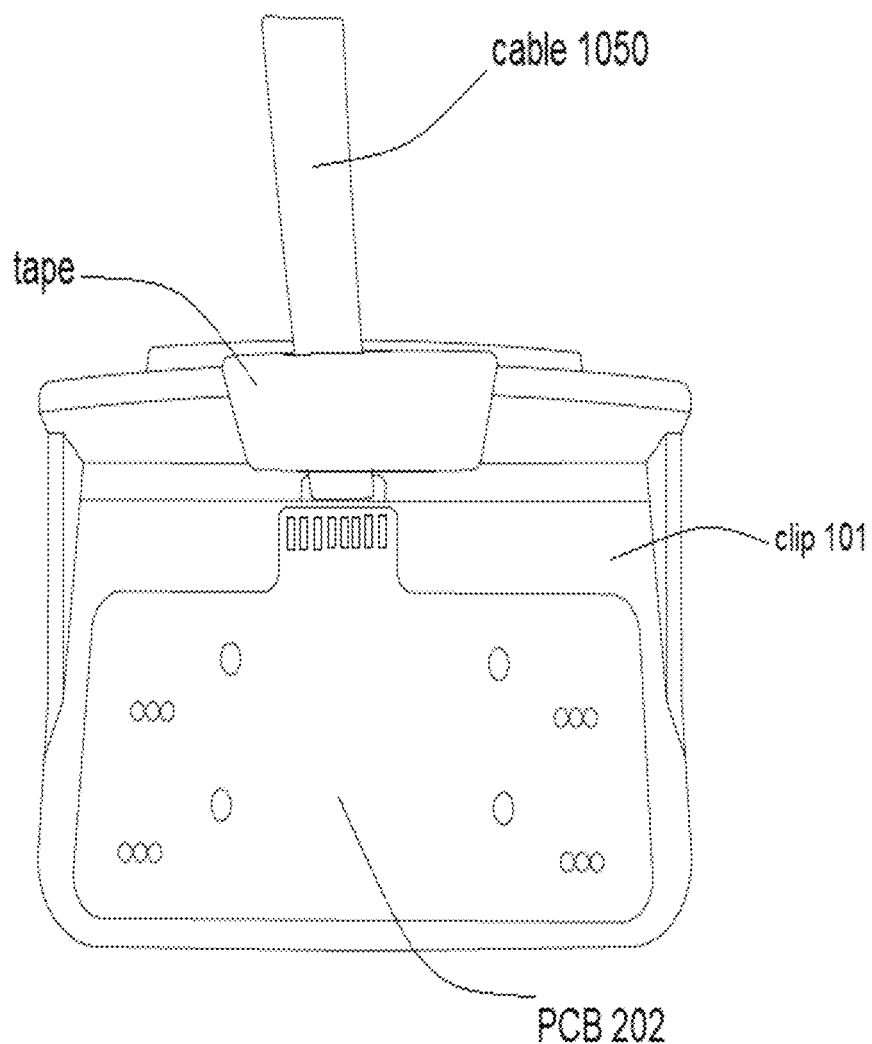
FIGS. 10B-10C show placement of a PCB into a recess within the housing, using tape to hold the flex cable flat against top of the clip.
Figure 10C:
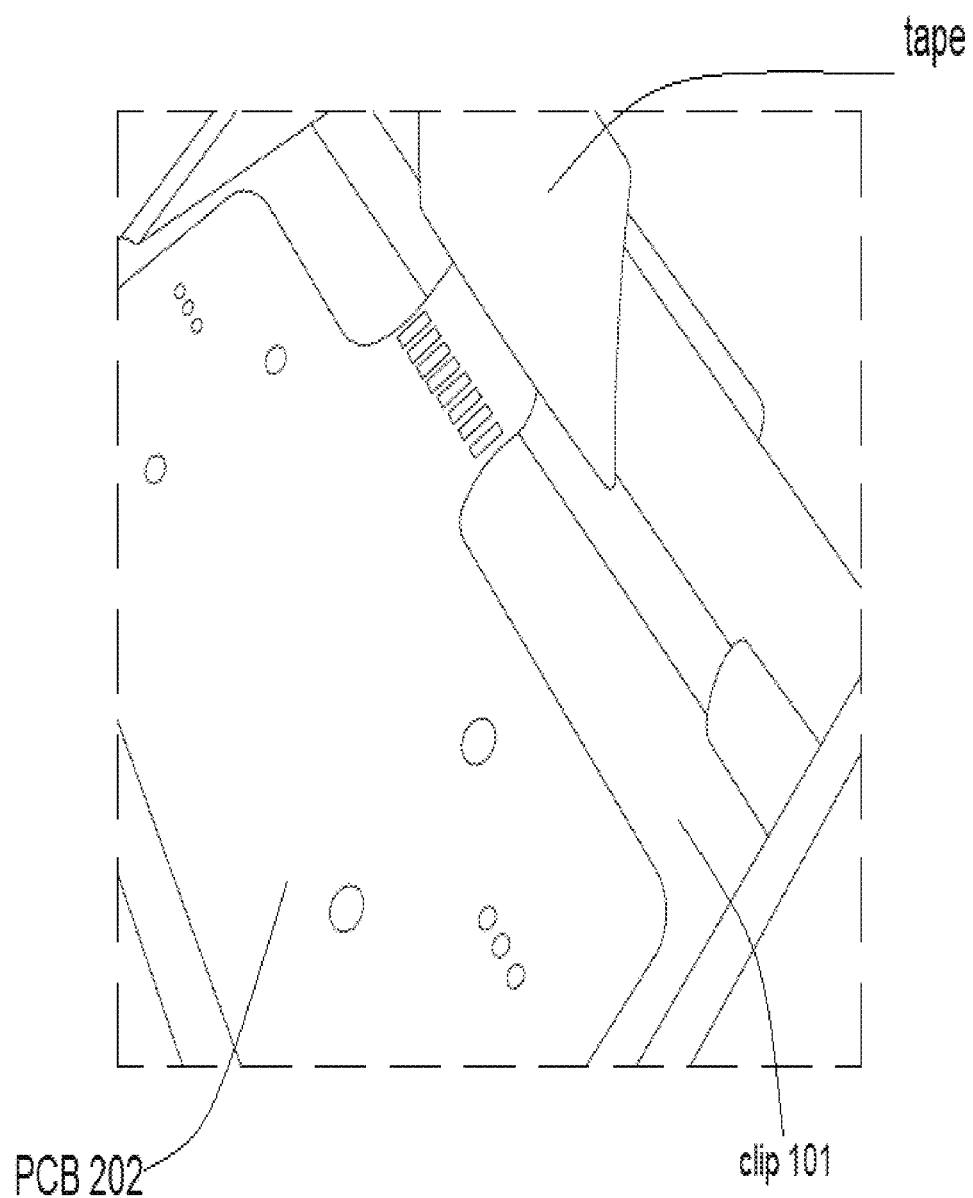

Apply adhesive, e.g. epoxy DP105 to e.g. six locations inside the housing 116. Then, place the PCB 202 in the recess 240, and as shown in FIGS. 10B-10C, use tape to hold the flex cable 1050 flat against top of the clip 101.

12) Initial Power Test and Programming Main Board
  Process overview
  Confirm no shorts
  Confirm communication to module
  Update firmware
  Cycle power
  Load program
  Temporarily connect a probe board and measure power
  Test T function
  12A). Connect a current limited DC power supply to the battery terminals 1220 and verify current is at a predetermined level;
  12B). Remove power and connect the cable to power; Use a customized proprietary loading resource (e.g. Uwterminal) to verify communication. This returns a firmware level.
  12C). Close the attachment port, and then disconnect the USB cable from the PCB 202;
  Reconnect power and run e.g. BL65xUartFwUpgrade.exe to load the firmware;
  12D). Disconnect power, and wait for a predetermined period;
  12E). Reconnect power and restart the loading resource (e.g. Uwterminal); obtain a module's specific address;
  12F). Connect a probe board;
  12G). Connect a dc power supply, verify idle current is around a predetermined amount, and verify a "connect" function (right button). High current (e.g. >100 uA) can indicate a problem. However, occasional spikes in current are normal.

12) (Continued) Initial Power Test and Programming Main Board
  DC Power connected to battery terminals;
  Tag-connect cable connected to a specific terminal on the PCB 202;
  Tag-connect cable connected to the adapter;

13) Module Housing Assembly

Figure 11A:
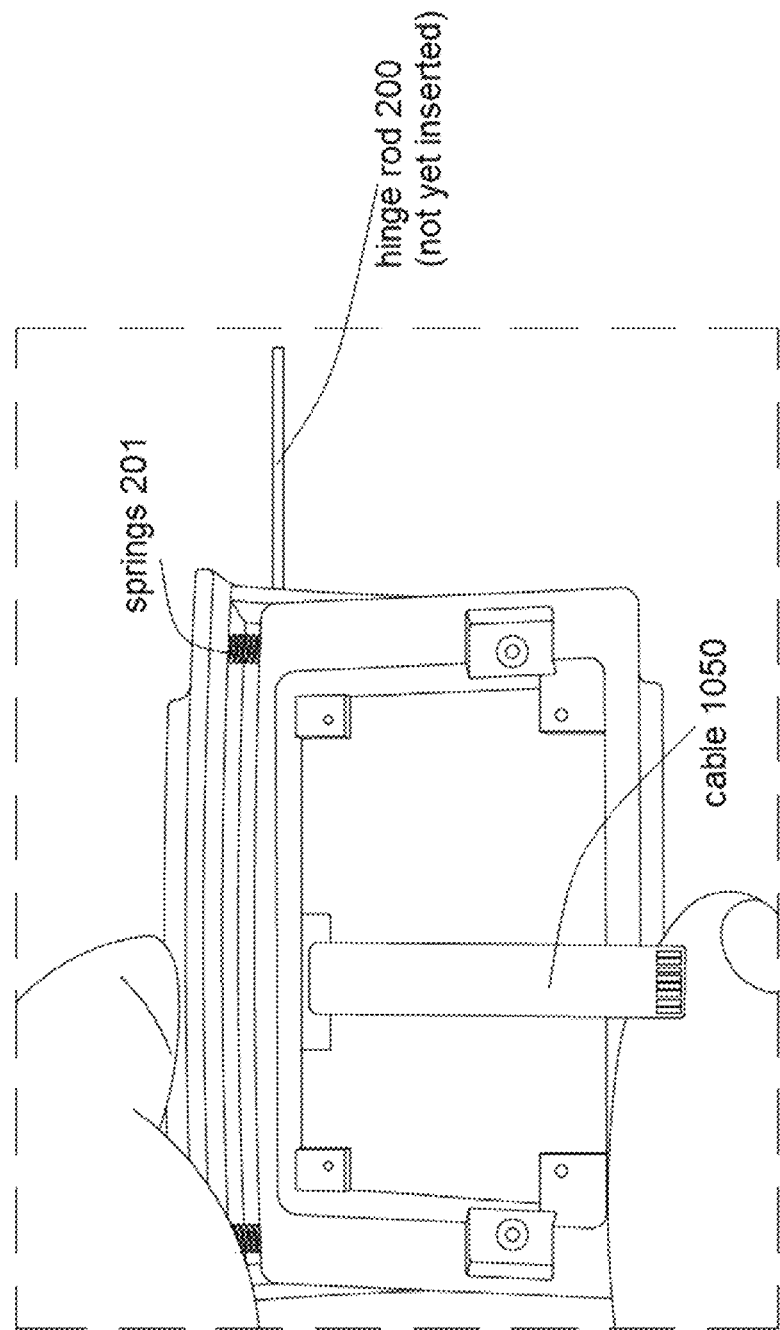
FIG. 11A shows a process of manually affirming that a flex cable is properly bonded to the clip while remaining free past a radius corner.
Figure 11B:
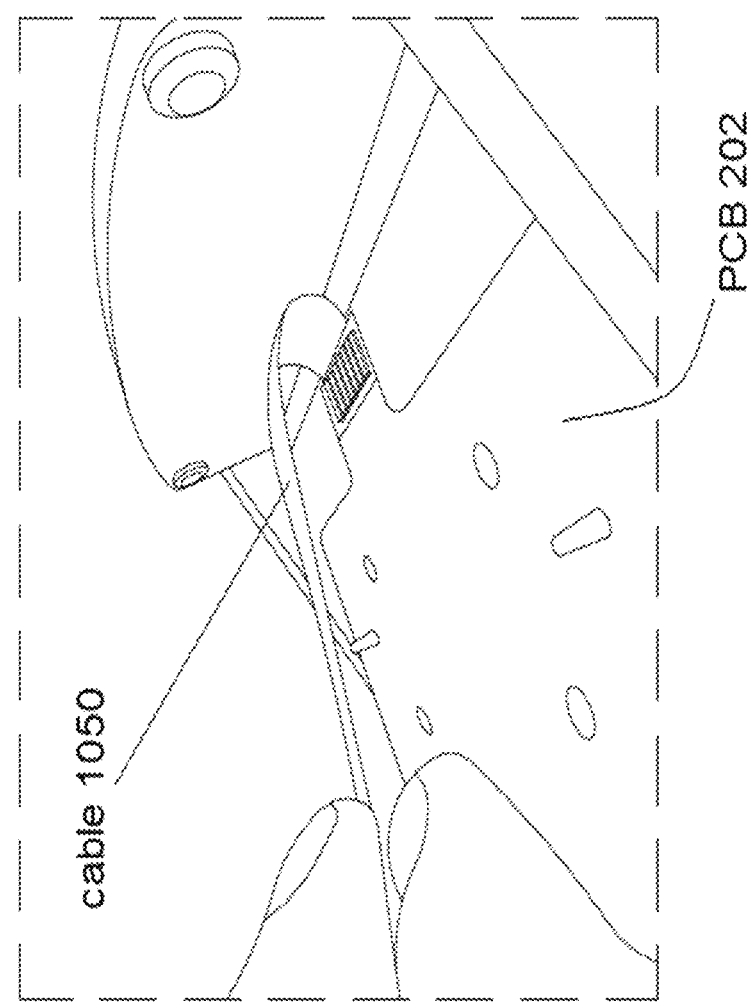
FIG. 11B shows a process of pulling the flex cable to free it from any possible contact with any adhesive.

As shown in FIG. 11A, affirm that the flex cable 1050 is properly bonded to the clip 101 while remaining free past a radius corner. As shown in FIG. 11B, gently pull the flex cable 1050 to free from adhesive if required. Test fit with the housing to verify flex passes over hinge rod 200 but is not pinched. Add the springs 201, pinch the housing into position and slide in hinge rod (tapered end first). Set the hinge rod 200 below surface to even (verb) an amount on the left and right sides. This will be later be heat-staked.

14) Main Board Install

Figure 12A:
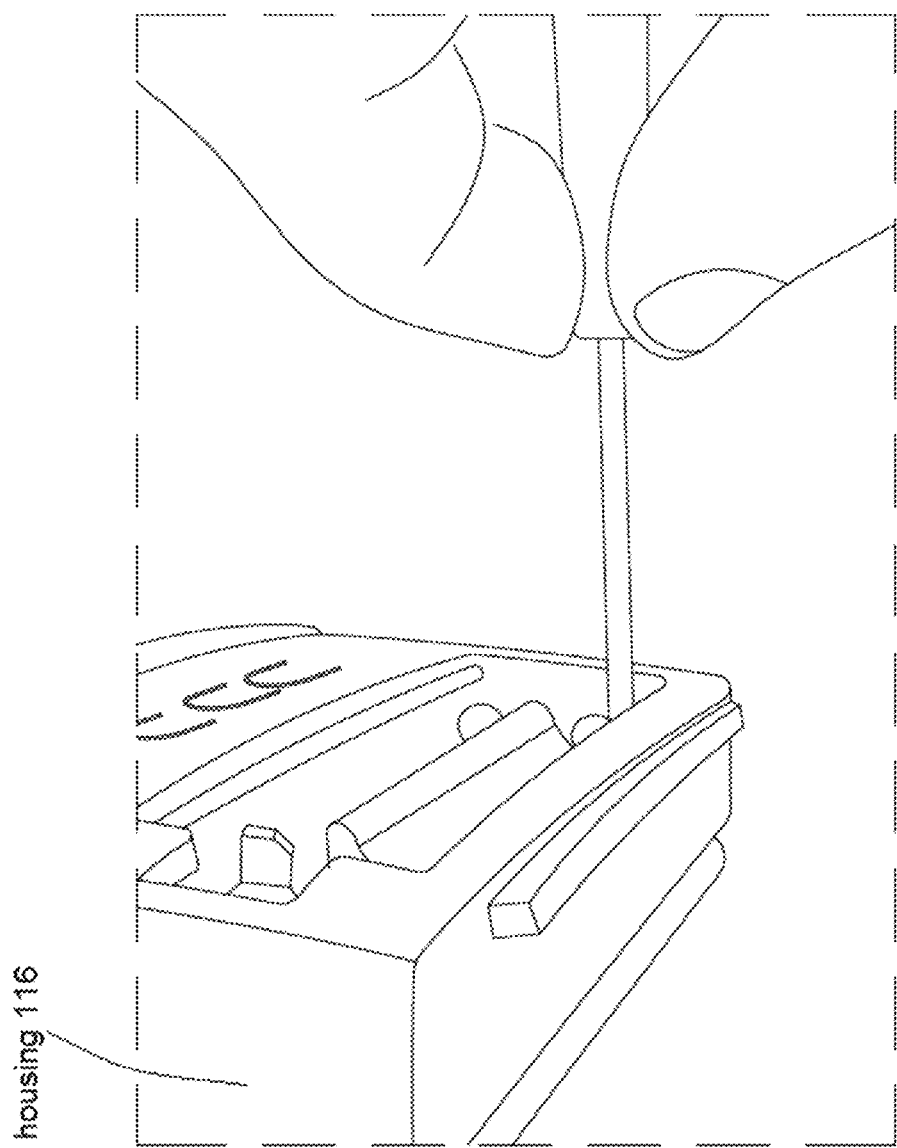
FIG. 12A shows installing of threading screws through a switch plate in the housing.
Figure 12B:
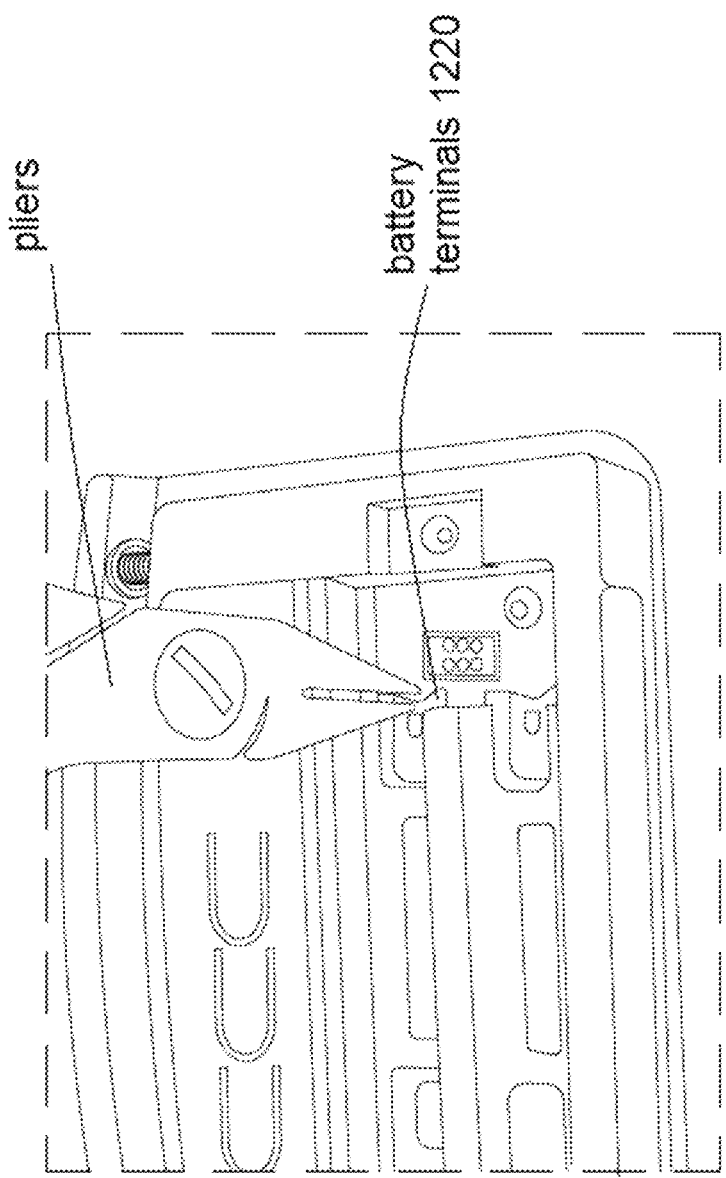
FIG. 12B shows bending of battery clips using pliers.
Figure 12C:
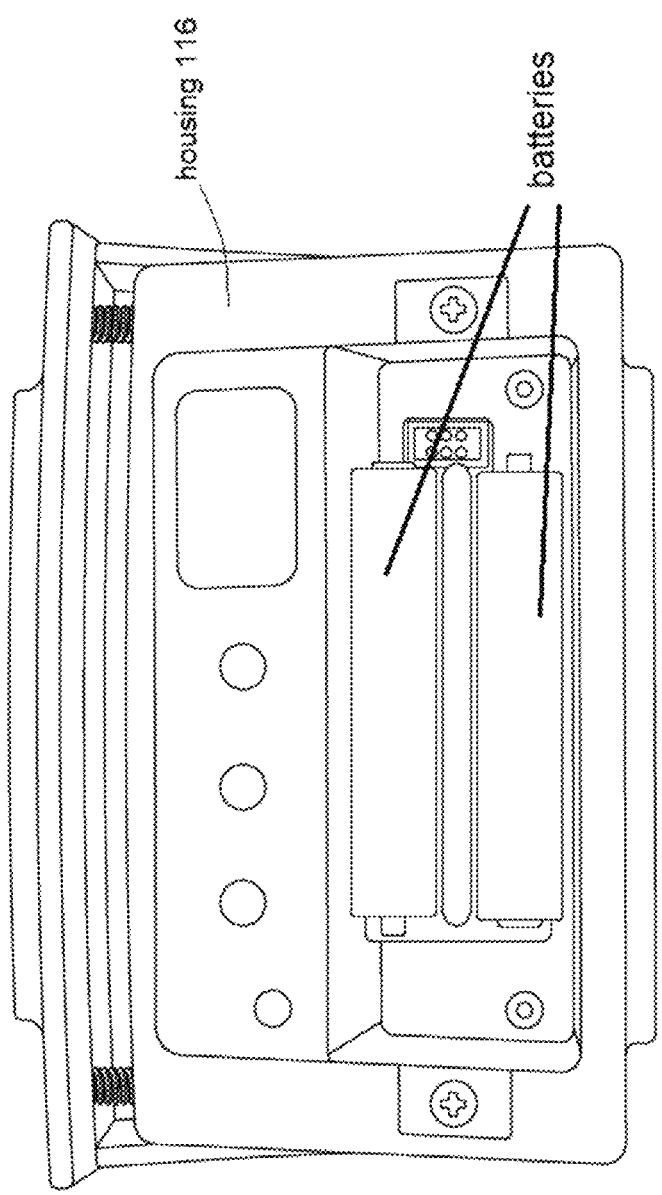
FIG. 12C shows an example installation of batteries within the battery clips.

Install the flex cable 1050 to a connector on the PCB 202. FIG. 12A shows installing of 4 threading screws through a switch plate in the housing 116. It is important to not overtighten the screws. Then, bend the battery clips 1220 to provide a snug connection, if required. As shown in FIG. 12B, one way to achieve this is using pliers. Connect the current-limited DC supply to verify a predetermined amount of current. Install the batteries (e.g. FIG. 12C) and test a section of the garment 510.

15) Functional Testing

In an embodiment, a specially-configured raspberry pi can be used to observe the wireless data leaving the module 100. In an embodiment, transmissions occur every 15 seconds, although this can be adjusted depending on the environment where the system 180 is employed. At 15 seconds/transmission, it will take a couple of minutes to complete the test process below.

It is best to powering one module 100 at a time makes is easy to observe the data. Otherwise the ID will need to be checked to know which module 100 transmitted the data.

Connect the raspberry pi to a monitor/keyboard/mouse to run a test program. Press T button (an LED will flash). Confirm position sensor by rotating module and observing a change in position data. Press button two and observe change in button data. Observe temperature is at present room temperature. Press shorting bar to garment 510 test strip (electrode 503) to emulate a garment-wetting event. Then, confirm a change in moisture data. Remove batteries and install the battery door 103.

16) Heat Stake the Hinge Rod 200

Figure 13:
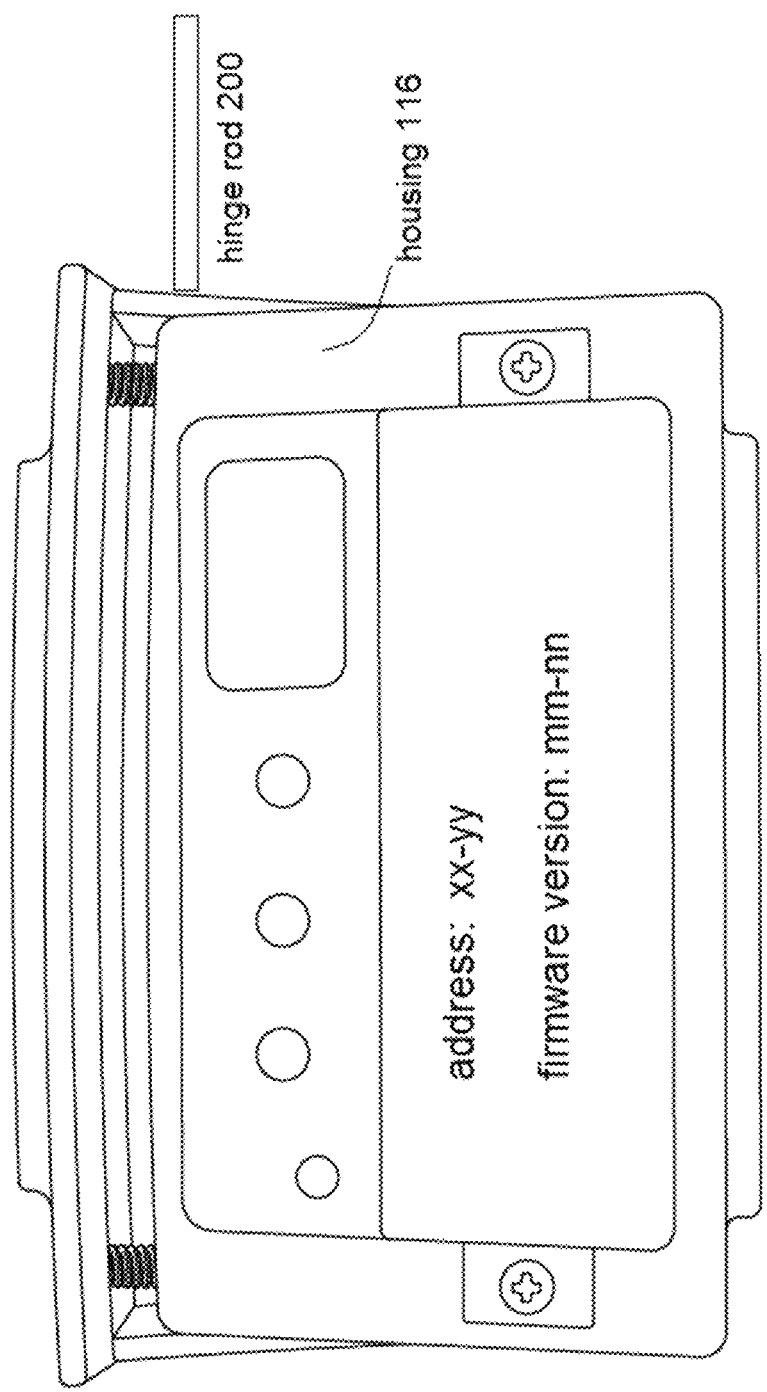
FIG. 13 shows an example marking of a module address and a firmware version onto the housing.

Use a soldering iron tool (provided) to melt plastic and thus hold the hinge rod 200 in place on both sides of the housing 116. As shown in FIG. 13, place a module address and the firmware version onto the housing 116.

DISCLAIMER

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A clip-on electronics module used with a garment containing a plurality of moisture sensing electrodes, comprising:
   a housing having a body cavity suitable for containing a battery and a plurality of electronics mounted on a printed circuit board (PCB);
   a movable clip portion attached to the housing, the movable clip portion configured to be placed over a waistband of the garment;
   a switch panel that covers switches and an LED indicator;
   a battery door for providing access to the battery within the module;
   a raised ridge on the bottom of the housing for providing tactile feedback and improving grip when squeezing the clip portion during attachment and removal and a raised ridge on the top of clip portion; and
   the clip portion and housing having predetermined contours, predetermined tapering, and alignment labeling for facilitating effective attachment to the garment and ensuring effective electrical contact with the moisture sensing electrodes within the garment;
   a plurality of coil springs located between the clip portion and the housing which provide a first clamping force for securing the housing to the garment;
   and which provide a second clamping force for a plurality of probes to contact the moisture-sensing electrodes within the garment;
   wherein the PCB containing the plurality of probes and a temperature sensor.

2. The module of claim 1, further comprising
   the garment being a shaped like a diaper and having the plurality of moisture sensing electrodes embedded therein.

3. The module of claim 1, further comprising
   a metal hinge rod which joins the housing with the clip portion and defines a location and axis of rotation of the housing.

4. The module of claim 1, further comprising:
   a spacer located near to the coil springs thereby providing an adjustable clamping force.

5. The module of claim 1, further comprising:
   one or more magnets, located near to the plurality of coil springs, to enhance the clamping force.

6. The module of claim 1, further comprising
   the predetermined tapering being angled so as to facilitate sliding of the module over the garment.

7. The module of claim 1, further comprising
   a plurality of backing strips suitable for giving the plurality of probes a firm but deformable surface to press into; and
   the tips of the plurality of probes each having a predetermined taper selected to achieve optimum penetration of the plurality of backing strips.

8. The module of claim 1, wherein a plurality of switches located on the module housing to allow a caregiver to press a switch for proper-attachment test, urine incontinence, or bowel incontinence.

9. The module of claim 8, wherein one or more of the plurality of switches having the ability to identify the caregiver as being physically present with a patient at a particular time.

10. The module of claim 8, further comprising:
    one or more of the switches being an attachment test switch configured to initiate a specific predetermined test sequence on the module.

11. The module of claim 1, further comprising
    an accelerometer, located within the PCB, which indicates a body position of a patient such that external computing resources can determine how much time the patient has spent in a particular body position and whether that patient had a fall.

12. The module of claim 1, further comprising
    a temperature sensor located in the clip portion which measures a surface temperature of a section of the clip portion which is in contact with skin of the wearer and which determines body temperature.

13. The module of claim 1, wherein the clip portion of the housing having access to the skin of a wearer, such that conductive contacts within the clip portion can be used to measure skin resistance and also verify module position against the skin.

14. The module of claim 1, wherein the housing has a labeling which provides a visual aid and assistance in aligning the module housing with the conductive strips within the garment.

15. The module of claim 1, the plurality of electronics further comprising:
    a BlueTooth Low Energy (BTLE) mechanism which sends BTLE advertisements, where the BTLE advertisements are configured to contain information regarding medical status of a wearer of a module.

16. The module of claim 15, further comprising
    the BTLE mechanism sending sensor and status data from the module to a computer network and patient database which encompasses multiple modules.

17. The module of claim 1, the plurality of electronics further comprising:
    a clock mechanism; and
    a low battery indicator configured to indicate both voltage used and time in service.

18. The module of claim 1, further comprising:
    the LED indicator can flash rather than stay on solid, thereby reducing power usage.

* * * * *